(12) United States Patent
Hassenpflug et al.

(10) Patent No.: US 10,548,778 B2
(45) Date of Patent: Feb. 4, 2020

(54) NEGATIVE PRESSURE PUMPS AND RELATED METHODS

(71) Applicant: IC Surgical, Inc., Grand Rapids, MI (US)

(72) Inventors: Eric Hassenpflug, Westerville, OH (US); John Bartholomew, Hilliard, OH (US); Steven Madland, Columbus, OH (US); David Holley, Lancaster, OH (US); John P. Tallarico, Powell, OH (US); Larry K. Hooks, Jr., Gahanna, OH (US); Corrie Bennison, Lewis Center, OH (US); William G. Atterbury, Columbus, OH (US); Michael Scott Ulrich, Columbus, OH (US); Russell Kittel, Gahanna, OH (US); Jeffrey L. Ellis, Columbus, OH (US); Thomas Haubert, Columbus, OH (US)

(73) Assignee: IC Surgical, Inc., Grand Rapids, MI (US)

( * ) Notice: Subject to any disclaimer, the term of this patent is extended or adjusted under 35 U.S.C. 154(b) by 0 days.

(21) Appl. No.: 16/371,376

(22) Filed: Apr. 1, 2019

(65) Prior Publication Data

US 2019/0298576 A1 Oct. 3, 2019

Related U.S. Application Data

(60) Provisional application No. 62/820,912, filed on Mar. 20, 2019, provisional application No. 62/651,407, filed on Apr. 2, 2018.

(51) Int. Cl.
*A61M 1/00* (2006.01)
*A61F 13/00* (2006.01)
(Continued)

(52) U.S. Cl.
CPC ..... *A61F 13/00068* (2013.01); *A61M 1/0023* (2013.01); *A61M 1/0068* (2014.02)

(58) Field of Classification Search
CPC ......... A61M 1/00; A61M 27/00; A61F 13/00; A61F 13/02; A61F 15/00
See application file for complete search history.

(56) References Cited

U.S. PATENT DOCUMENTS 3,447,479 A * 6/1969 Rosenberg ............. A61M 3/00
417/271
3,841,331 A * 10/1974 Wilder ................ A61M 1/0066
604/152
(Continued)

FOREIGN PATENT DOCUMENTS

WO WO 2010/006182 A2 1/2010

OTHER PUBLICATIONS

SNAP Therapy System "Silent Cartridge Technology" Acelity, (3 pages).

*Primary Examiner* — Tatyana Zalukaeva
*Assistant Examiner* — Ilya Y Treyger
(74) *Attorney, Agent, or Firm* — Bookoff McAndrews, PLLC

(57) ABSTRACT

Devices and systems disclosed herein may include a negative pressure pump that includes a reservoir defining a lumen and a longitudinal axis, a piston, and a drive assembly comprising a spring. Motion of the spring may move the piston along the longitudinal axis of the reservoir to create a negative pressure within the reservoir. Methods of manufacturing a negative pressure pump and using a negative pressure pump to remove fluid from a target site are also described.

17 Claims, 23 Drawing Sheets

(51) Int. Cl.
*A61M 27/00* (2006.01)
*A61F 13/02* (2006.01)
*A61F 15/00* (2006.01)

(56) References Cited

U.S. PATENT DOCUMENTS

| | | | |
|---|---|---|---|
| 5,011,381 A * | 4/1991 | Neward | F04B 7/00 417/440 |
| 6,129,181 A | 10/2000 | Weems | |
| 6,669,668 B1 | 12/2003 | Kleeman et al. | |
| 6,685,681 B2 * | 2/2004 | Lockwood | A61M 1/0058 502/43 |
| 6,945,979 B2 | 9/2005 | Kortenbach et al. | |
| 7,156,803 B2 | 1/2007 | Voellmicke et al. | |
| D544,092 S | 6/2007 | Lewis | |
| 7,232,266 B2 | 6/2007 | Giese | |
| D547,438 S | 7/2007 | Lewis | |
| D565,177 S | 3/2008 | Locke et al. | |
| D581,042 S | 11/2008 | Randolph et al. | |
| D581,521 S | 11/2008 | Locke et al. | |
| D581,522 S | 11/2008 | Randolph et al. | |
| D590,934 S | 4/2009 | Randolph et al. | |
| D602,583 S | 10/2009 | Pidgeon et al. | |
| D614,284 S | 4/2010 | Mormino et al. | |
| D618,337 S | 6/2010 | Pratt et al. | |
| D624,177 S | 9/2010 | Pratt et al. | |
| D625,801 S | 10/2010 | Pidgeon et al. | |
| D629,502 S | 12/2010 | Au et al. | |
| 8,007,257 B2 | 8/2011 | Heaton et al. | |
| 8,128,607 B2 | 3/2012 | Hu et al. | |
| 8,162,908 B2 | 4/2012 | Hu et al. | |
| 8,177,764 B2 | 5/2012 | Hu et al. | |
| 8,287,507 B2 | 10/2012 | Heaton et al. | |
| 8,323,264 B2 | 12/2012 | Weston et al. | |
| 8,337,474 B2 | 12/2012 | Hu et al. | |
| 8,366,644 B2 | 2/2013 | Coward et al. | |
| 8,377,043 B2 | 2/2013 | Kriesel et al. | |
| 8,394,081 B2 | 3/2013 | Locke et al. | |
| 8,435,221 B2 | 5/2013 | Hu et al. | |
| D686,724 S | 7/2013 | Au et al. | |
| D687,537 S | 8/2013 | Au et al. | |
| 8,535,283 B2 | 9/2013 | Heaton et al. | |
| 8,556,805 B2 | 10/2013 | Hashimoto et al. | |
| 8,569,566 B2 | 10/2013 | Blott et al. | |
| 8,622,965 B2 | 1/2014 | Kriesel | |
| 8,641,692 B2 | 2/2014 | Tout et al. | |
| 8,663,199 B2 | 3/2014 | Jaeb et al. | |
| 8,679,079 B2 | 3/2014 | Heaton et al. | |
| 8,689,646 B2 | 4/2014 | Carr | |
| 8,702,665 B2 | 4/2014 | Locke et al. | |
| 8,728,045 B2 | 5/2014 | Hu et al. | |
| 8,728,046 B2 | 5/2014 | Hu et al. | |
| 8,753,322 B2 | 6/2014 | Hu et al. | |
| D712,024 S | 8/2014 | Au et al. | |
| 8,795,246 B2 | 8/2014 | Hu et al. | |
| 8,808,259 B2 | 8/2014 | Walton et al. | |
| 8,852,170 B2 | 10/2014 | Weston et al. | |
| 8,858,516 B2 | 10/2014 | Hu et al. | |
| 8,864,748 B2 | 10/2014 | Coulthard et al. | |
| 8,876,861 B2 | 11/2014 | Green et al. | |
| 8,926,575 B2 | 1/2015 | Hu et al. | |
| 8,961,481 B2 | 2/2015 | Hu et al. | |
| 8,968,272 B2 | 3/2015 | Khouri et al. | |
| 8,986,267 B2 | 3/2015 | Heaton et al. | |
| 8,992,494 B2 | 3/2015 | Pratt et al. | |
| 9,028,458 B2 | 5/2015 | Heaton et al. | |
| 9,084,845 B2 | 7/2015 | Adie et al. | |
| 9,089,676 B2 | 7/2015 | Locke et al. | |
| 9,180,231 B2 | 11/2015 | Greener | |
| 9,215,964 B2 | 12/2015 | Loske | |
| 9,283,307 B2 | 3/2016 | Hu et al. | |
| 9,345,821 B2 | 5/2016 | Locke et al. | |
| 9,375,521 B2 | 6/2016 | Hudspeth et al. | |
| 9,545,466 B2 | 1/2017 | Locke et al. | |
| 9,561,312 B2 | 2/2017 | Heaton et al. | |
| 9,579,430 B2 | 2/2017 | Hu et al. | |
| 9,597,079 B2 | 3/2017 | Elliott et al. | |
| 9,656,007 B2 | 5/2017 | Tout et al. | |
| 9,744,275 B2 | 8/2017 | Khouri et al. | |
| 9,839,727 B2 | 12/2017 | Anderson et al. | |
| 9,844,485 B2 | 12/2017 | Locke et al. | |
| 9,855,123 B2 | 1/2018 | Wolgin | |
| 9,872,974 B2 | 1/2018 | Locke et al. | |
| 9,889,240 B2 | 2/2018 | Locke et al. | |
| 9,889,241 B2 | 2/2018 | Vess et al. | |
| 9,895,471 B2 | 2/2018 | Hu et al. | |
| 2014/0276498 A1 | 9/2014 | Connor et al. | |
| 2017/0224885 A1 | 8/2017 | Conner et al. | |
| 2018/0001000 A1 | 1/2018 | Herwig et al. | |

\* cited by examiner

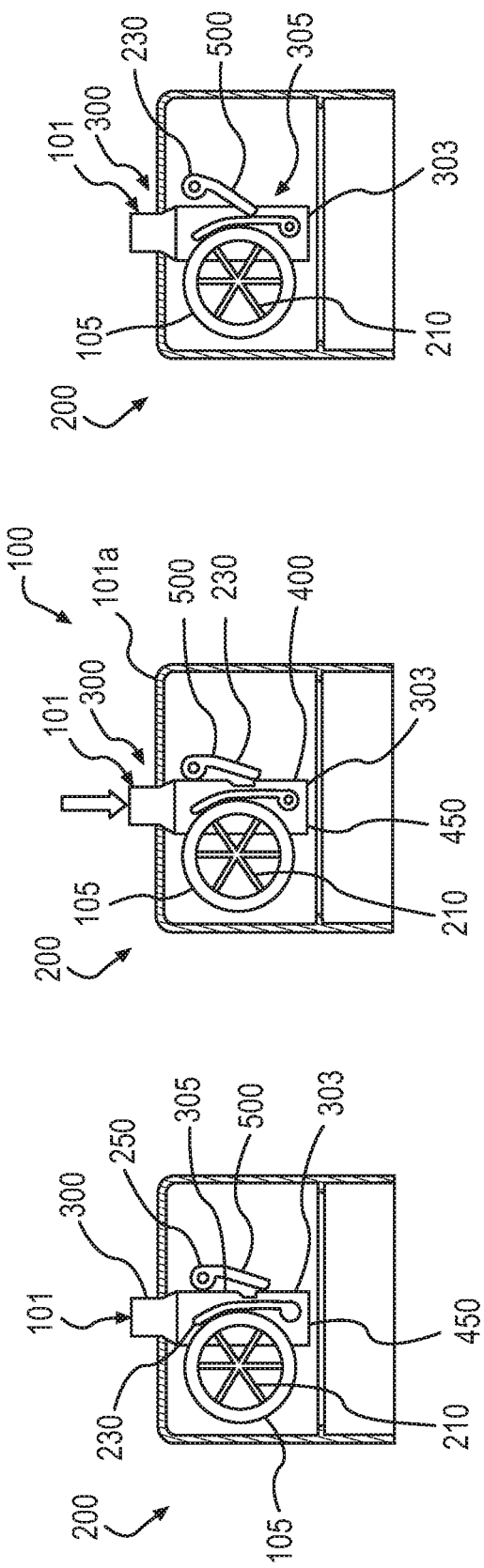

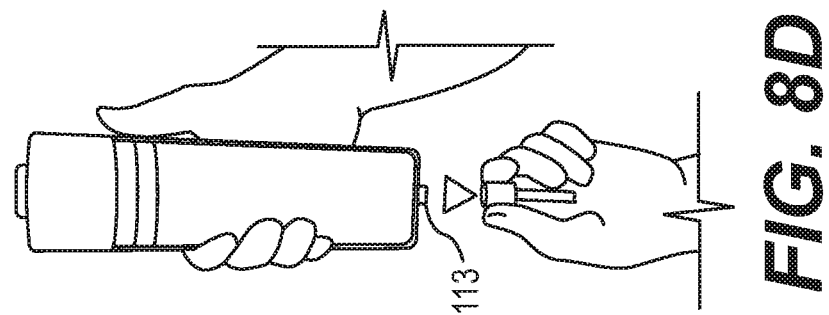
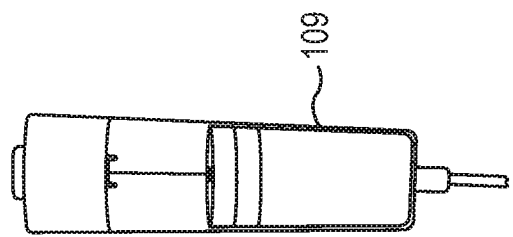
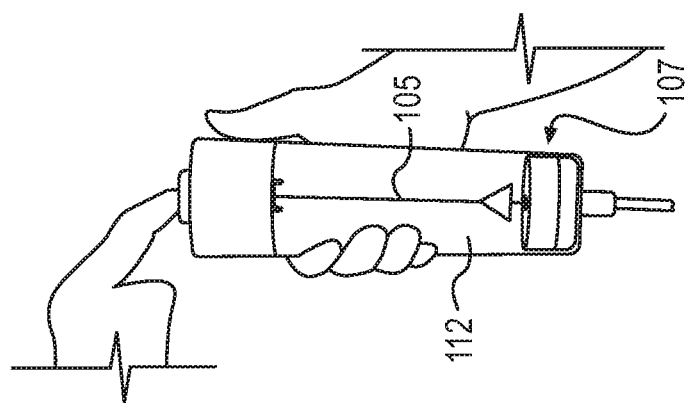
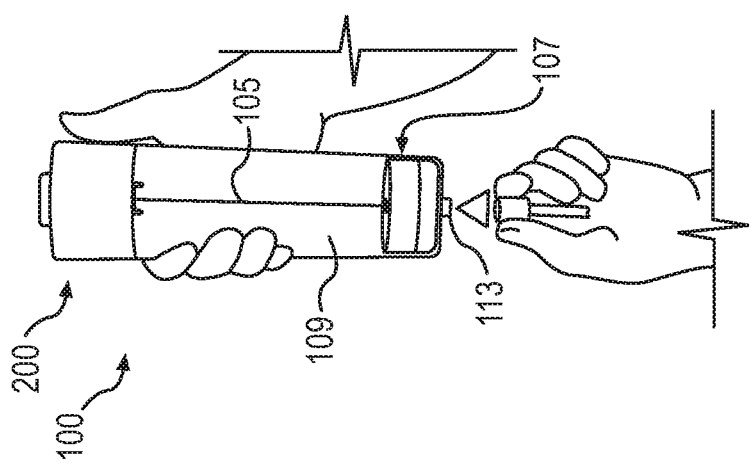

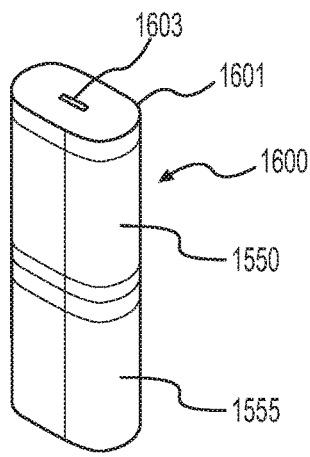
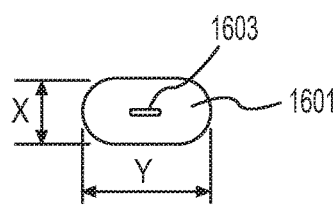
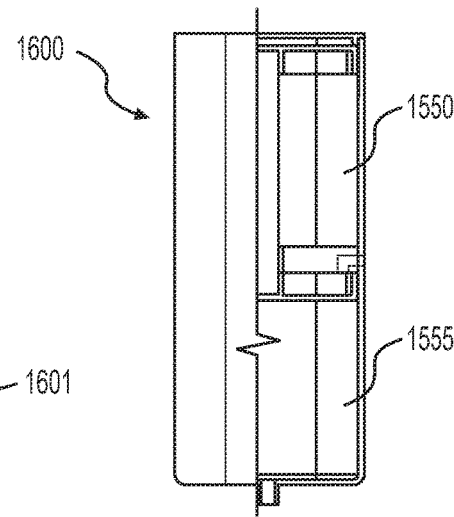
FIG. 13A   FIG. 13B   FIG. 13C
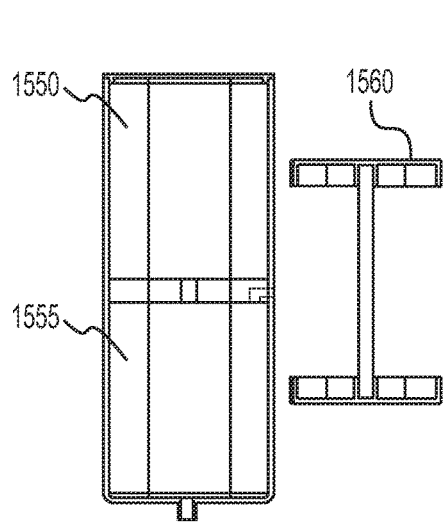
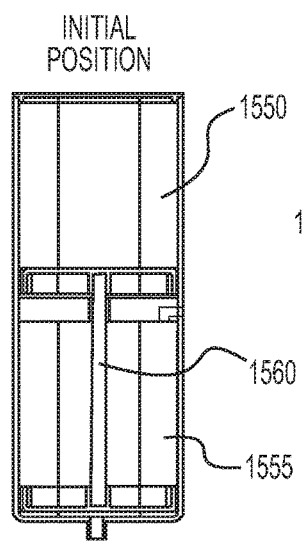
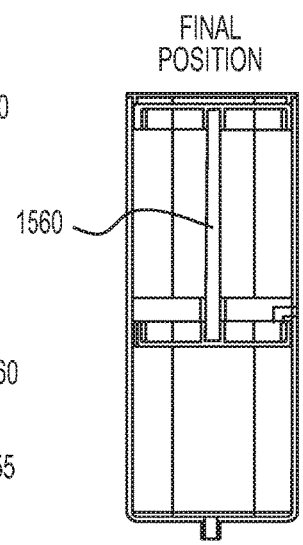
FIG. 13D   FIG. 13E   FIG. 13F

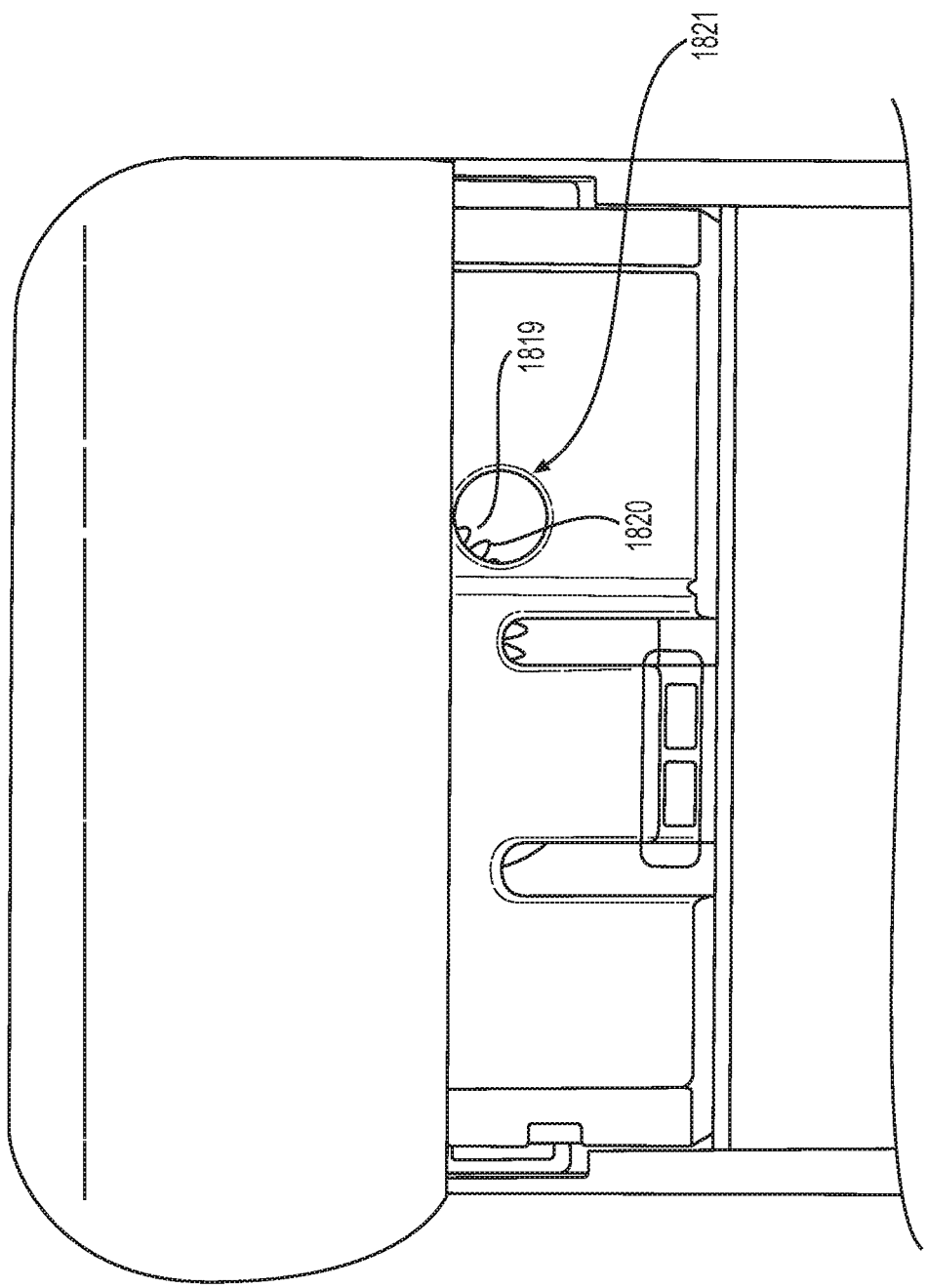

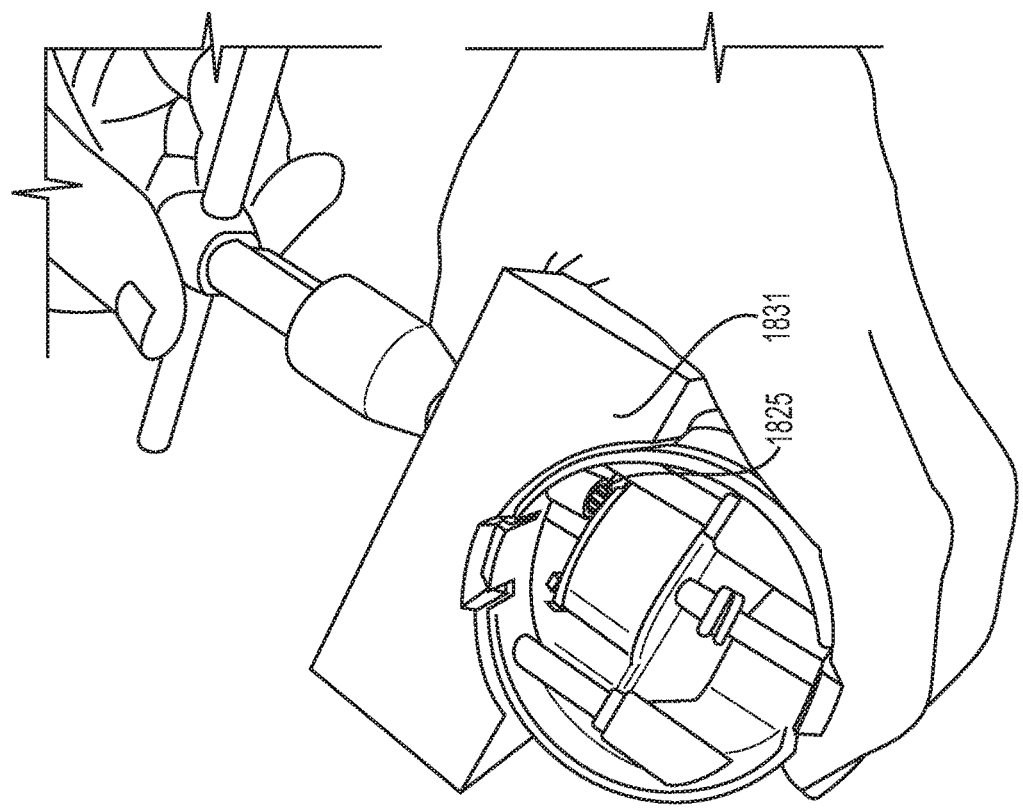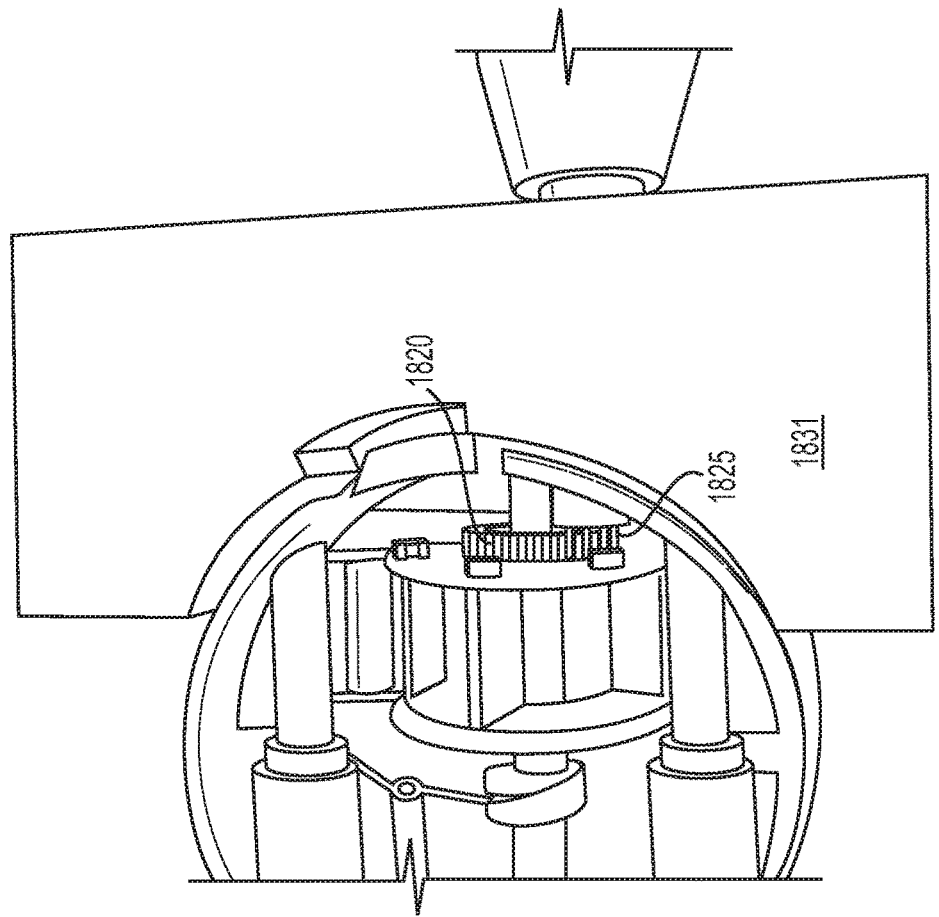
FIG. 14I

NEGATIVE PRESSURE PUMPS AND RELATED METHODS

CROSS-REFERENCE TO RELATED APPLICATIONS

This patent application claims the benefit under 35 U.S.C. § 119 to U.S. Provisional Patent Application No. 62/651,407 filed on Apr. 2, 2018, and U.S. Provisional Patent Application No. 62/820,912 filed on Mar. 20, 2019, the entireties of which are incorporated herein by reference.

TECHNICAL FIELD

The present disclosure relates to a negative pressure pump. The pump may be used for internal or external wounds or for other medical and/or nonmedical applications.

INTRODUCTION

Circumstances can arise wherein an undesirable buildup of fluid may be removed. For example, in medical procedures, fluid may pool at the treatment site of a patient before, after, or during a procedure. Removal of the fluid may facilitate healing, e.g., at the treatment site, or otherwise promote the health of the patient. Accordingly, a desire exists for devices and methods for drawing fluids away from a site in an effective, low-cost manner.

SUMMARY

Some embodiments of the present disclosure are directed to a disposable negative pressure pump comprising a reservoir comprising an inner wall that defines a lumen along a longitudinal axis of the reservoir, a drive assembly coupled to the reservoir, the drive assembly comprising a spring, a piston forming a seal against the inner wall of the reservoir and slidable within the lumen along the longitudinal axis; and a cable extending through the lumen, the cable having a first end coupled to the drive assembly and a second end coupled to the piston, wherein sliding the piston along the reservoir via the drive assembly creates a negative pressure within the lumen. The reservoir may have a constant cross-sectional dimension along an entire length of the reservoir and the cable may be coupled to the drive assembly at a cable attachment point. Further, the drive assembly may comprise a first drum and a second drum, where the cable attachment point may be on the second drum. The spring may be coupled to the second drum, or coupled to each of the first drum and the second drum. In at least one embodiment, winding of the spring onto the first drum may cause winding of the cable onto the second drum, and winding of the cable onto the second drum may move the piston along the longitudinal axis of the reservoir. A medical system for removing fluid from a target site may comprise a patient therapy unit comprising a manifold and the above-described negative pressure pump.

Embodiments of the present disclosure also are directed to a method of removing fluid from a target site, the method comprising: placing a first end of a manifold at the target site, wherein a second end of the manifold is coupled to a negative pressure pump comprising: a reservoir comprising an inner wall that defines a lumen along a longitudinal axis of the reservoir, the manifold being in communication with the reservoir; a drive assembly coupled to the reservoir and comprising a spring; and a piston coupled to the drive assembly, the piston having a cross-sectional dimension corresponding to a cross-sectional dimension of the reservoir; and initiating the drive assembly of the negative pressure pump, wherein motion of the spring moves the piston within the lumen to create a negative pressure within the reservoir. The target site may be an internal wound, an external wound, any location on a patient, or any location related to a patient. A location on a patient may include a location within the patient's body, a location on a patient's skin, a patient treatment site (which may not necessarily be a wound), a surgical site, etc. A location related to a patient may include an apparatus or device used in patient treatment, a surgical site, a clinical study site, etc. The spring may be comprised of a torsion spring.

The piston may be spaced from the drive assembly along the longitudinal axis of the reservoir before initiating the drive assembly and the piston may be adjacent to the drive assembly after initiating the drive assembly. In at least one embodiment, the drive assembly may be coupled to the piston by a cable extending along the longitudinal axis, and the drive assembly may further comprise a first drum and a second drum. The cable may be coupled to the second drum, and the spring may engage each of the first drum and the second drum when the drive assembly is initialized.

Embodiments of the present disclosure also include a method of manufacturing a negative pressure pump, the method comprising: biasing a spring of the drive assembly to wind from a first drum to a second drum, wherein the reservoir of the negative pressure pump comprises an inner wall that defines a lumen along a longitudinal axis of the reservoir, the drive assembly being coupled to the reservoir, and wherein the drive assembly is coupled to the piston by a cable extending through the lumen of the reservoir. The biasing may include winding the spring on the second drum and locking the spring into a biased position. Alternatively or in addition, the biasing may include accessing a spring winding gear of the drive assembly via a gear access hole, and possibly sealing the gear access hole after biasing the spring.

BRIEF DESCRIPTION OF THE DRAWINGS

The accompanying drawings, which are incorporated into and constitute a part of this specification, illustrate various exemplary embodiments and, together with the description, serve to explain the principles of the present disclosure. The drawings show different aspects of the present disclosure and, where appropriate, reference numerals illustrating like structures, components, materials and/or elements in different figures are labeled similarly. It is understood that various combinations and/or omissions of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended to reflect or indicate that the embodiment(s) is/are "example" embodiment(s).

FIGS. 7A-7C depict exemplary operation of a drive assembly, according to the second embodiment of the present disclosure.

FIGS. 8A-8D provide an exemplary method of using a disposable negative pressure pump, according to an embodiment of the present disclosure.

FIGS. 13A-13F provide various views of an exemplary pressure-actuated negative pressure pump, according to an embodiment of the present disclosure.

FIGS. 14G-FIG. 14I provide views of exemplary mechanisms for energizing the respective constant torque springs of the negative pressure pumps of FIGS. 14A and 14B, according to one embodiment of the present disclosure.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items.

DETAILED DESCRIPTION

Embodiments of the present disclosure relate to a pump, e.g., a negative pressure pump, which may be used to remove fluids from a target site. The pump may include a drive mechanism and a reservoir. In use, a tubing manifold may be connected to the reservoir and the pump may be used by a to provide negative pressure at the target site to promote. For example, a medical professional may use the pump to remove fluids from a patient, e.g., to promoting healing. The drive mechanism may create a negative pressure chamber in the reservoir, thus drawing fluids into the reservoir. The present disclosure describes various embodiments, including spring-actuated and pressure-actuated negative pressure pump devices.

A first embodiment of the spring-actuated mechanical negative pressure pump may include a reusable mechanical drive mechanism coupled to a disposable reservoir. A second embodiment of the spring-actuated mechanical negative pressure pump may include an entirely disposable negative pressure pump (where both a mechanical drive mechanism and reservoir may be disposable). The pressure-actuated negative pressure pump of a further embodiment may include a gas/pressure-based drive mechanism. For example, this embodiment may use a change in gas pressure to move a plunger through a reservoir to generate negative pressure (e.g., a pressure range from 100 mmHg to 760 mmHg in a chamber or reservoir of the pump), rather than using mechanical energy. At least a portion of the pressure-actuated negative pressure pump may be disposable. These and other aspects of the present disclosure are described in greater detail below.

Figure 1:
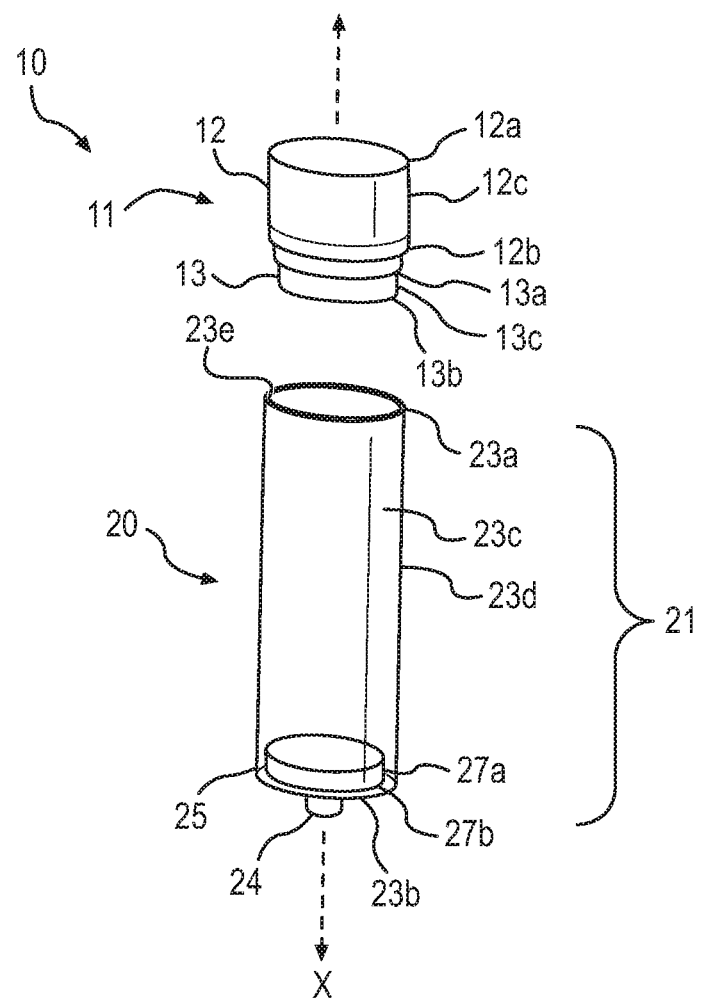
FIG. 1 provides an exploded view of an exemplary negative pressure pump's reusable drive unit and a disposable reservoir, according to one embodiment of the present disclosure.

As shown in FIG. 1, a first embodiment of a negative pressure pump 10 with a disposable reservoir may include a reusable drive unit 11 and a reservoir 20 arranged along a central, longitudinal axis x. The reusable drive unit 11 may include a drive housing 12 and a carrier 13. Drive housing 12 may be of any suitable cross-sectional configuration, including, but not limited to, rectangular, circular, elliptical, triangular, or oval. Drive housing 12 may be comprised of suitable material, including, but not limited to, glass, plastic, metal, rubber, silicone, or a combination thereof. At least a portion of drive housing 12 may be opaque, transparent, or translucent. For example, drive housing 12 may include one or more transparent/translucent openings or windows that permit visualization of the contents of drive housing 12 (described in detail in FIGS. 2A-2D).

Drive housing 12 may include a first end 12a and a second end 12b, joined by an elongate surface 12c. The first end 12a, second end 12b, and elongate surface 12c may form the outer surface of drive housing 12. In one embodiment, the first end 12a or elongate surface 12c may include an activation mechanism for reusable drive unit 11 (e.g., a button or switch). In one embodiment, second end 12b of the drive housing 12 may include a rim that may receive carrier 13.

Drive housing 12 may be coupled to carrier 13. In one embodiment, a spring or wire (not shown) may extend from drive housing 12 to carrier 13. For example, the spring or wire may extend through at least a portion of the length of carrier 13 such that carrier 13 may be disposed at the end of the spring or wire (as described at FIG. 2D).

In one embodiment, the cross-section of carrier 13 may have the same shape as drive housing 12 (e.g., rectangular, circular, elliptical, triangular, oval, etc.). Carrier 13 may include a first portion 13a and a second portion 13b. In one embodiment, carrier 13 may be shaped so that the first portion 13a is concentric with the second end 12b of drive housing 12. For example, drive housing 12 may include a rim that extends past the first portion 13a of carrier 13, towards the second portion 13b of carrier 13. In this way, drive housing 12 may at least partially encase carrier 13.

In one embodiment, the first portion 13a of the carrier 13 may form a seal against drive housing 12's second end 12b. For example, the first portion 13a of carrier 13 may be at a default (e.g., storage) position flush against second end 12b of drive housing 12. In one embodiment, drive housing 12 and carrier 13 may include interlocking features that may secure carrier 13 to drive housing 12. In one embodiment, the first portion 13a may also be sized to fit inside reservoir 20.

In one embodiment, at least a portion of the second portion 13b may have the same cross-sectional shape as drive housing 12 and first portion 13a. The second portion 13b may be sized to fit inside a plunger 25. In one embodiment, the first portion 13a may be larger than second portion 13b. For example, ledge 13c may exist between first portion 13a and second portion 13b, due to the first portion 13a being larger than second portion 13b. The drive mechanisms of drive unit 11 are further described in FIGS. 2A-2D.

In one embodiment, fluid reservoir 20 may be joined to reusable drive unit 11. For example, at least a portion of drive housing 12 may be attached to reservoir 20, and carrier 13 may be disposed inside a lumen of reservoir 20. Reservoir 20 may be a hollow receptacle of any suitable cross-sectional configuration, including, but not limited to, rectangular, circular, elliptical, triangular, or oval. In one embodiment, the cross-sectional shape of reservoir 20 may correspond to the cross-sectional shape of drive housing 12. The cross-sectional size and shape of reservoir 20 may be consistent throughout the length of reservoir 20 (with the exception of manifold connector 24, as explained in further detail below). For example, the reservoir 20 may have or be arranged along a longitudinal axis, and the reservoir 20 may have a consistent cross-sectional shape along the length of the longitudinal axis. For example, the reservoir 20 may be cylindrical with a consistent diameter along the longitudinal axis of the reservoir 20. Other shapes of the reservoir 20 are contemplated and encompassed herein, e.g., other polygonal shapes such as rectangular, triangular, etc. Reservoir 20 may be comprised of disposable material, including, but not limited to, glass, plastic, metal, rubber, silicone, or a combination thereof. At least a portion of reservoir 20 may be opaque, transparent (to see contents therein), or translucent. In one embodiment, the outer surface of reservoir 20 may further include markings or indicators, for instance, indicating volume. Reservoir 20 may further include anti-slip coatings, ridges, protrusions, adhesives, or a combination thereof for ease of handling.

Reservoir 20 may include a housing 21, a manifold connector 24, and a plunger 25. In one embodiment, housing 21 may include a first end 23a and a second end 23b, joined by a wall 23c. First end 23a may include an opening to reservoir 20. In at least one embodiment, the first end 23a may abut the second end 12b of drive housing 12. The first end 23a of reservoir 20 may be secured to the second end 12b of drive housing 12. For example, first end 23a and second end 12b may include interlocking parts, threads, or surfaces that align against or within each other. The first end 23a and second end 12b may form a seal (e.g., using an o-ring) so that contents of reservoir 20 cannot escape or leak out of reservoir 20 when the first end 23a and second end 12b are in contact.

In at least one embodiment, the second end 23b may close off reservoir 20. First end 23a may include a hollow or open cross-section of reservoir 20, and second end 23b may include a solid surface in the shape of the cross-section of reservoir 20. In at least one embodiment, the first end 23a and second end 23b may share the same cross-sectional shape and/or size.

In at least one embodiment, the second end 23b may include manifold connector 24. Manifold connector 24 may comprise a lumen that contains a valve, e.g., a one-way valve. During use of the negative pressure pump 10, a manifold may be attached to manifold connector 24. The attachment may connect (e.g., provide fluid communication between) the target site, e.g., inside of a patient, and the inner chamber of reservoir 20 (formed by the first end 23a, second end 23b, and wall 23c).

In at least one embodiment, wall 23c may form a lumen of housing 21. Wall 23c may include an outer surface 23d and inner surface 23e. Anti-slip coatings, ridges, protrusions, and adhesives may be disposed on outer surface 23d. Inner surface 23e may form the lumen or inner chamber of reservoir 20. The inner surface 23e may have a cross-section that corresponds to or matches the cross-section of outer surface 23d. In at least one embodiment, inner surface 23e may include a smooth surface.

In at least one embodiment, reservoir 20 may further contain plunger 25. Plunger 25 may include a wall 27a aligned with axis x, and a base 27b transverse to axis x. Plunger wall 27a may have a cross-section corresponding to the reservoir inner surface 23e and/or the second portion 13b of carrier 13. Plunger wall 27a may be attached to plunger base 27b. Plunger base 27b may seal the lumen formed by plunger wall 27a from an area of reservoir 20 beneath plunger 25 (as viewed in FIGS. 4E-4G).

In at least one embodiment, reservoir second end 23b and reservoir inner surface 23e may contain plunger 25 within the lumen of reservoir 20. In particular, plunger base 27b may contact a reservoir base located at reservoir second end 23b when the reservoir is in an unused, storage, or default position. When the reservoir is in use, plunger 25 may slide along the reservoir inner surface 23e. In at least one embodiment, plunger wall 27a may be in direct contact, e.g., constant contact, with reservoir inner surface 23e, for instance, the outer surface of plunger wall 27a may lie against the reservoir inner surface 23e. Alternatively, plunger wall 27a may have an O-ring or other seal around it to ride against the reservoir wall 23c.

Figure 3A:
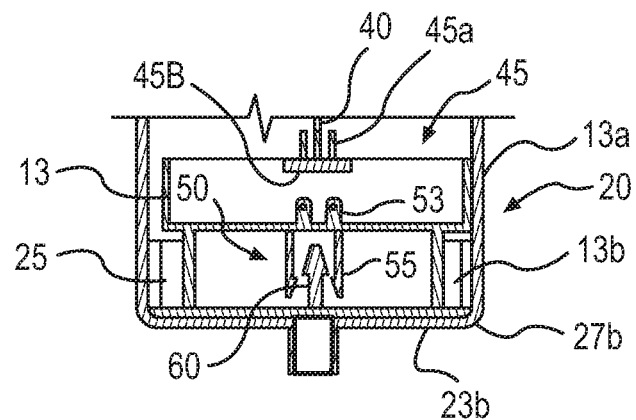
FIGS. 3A-3C provide various views of an exemplary locking mechanism that may secure a reusable drive unit to a disposable reservoir, according to one embodiment of the present disclosure.
Figure 3B:
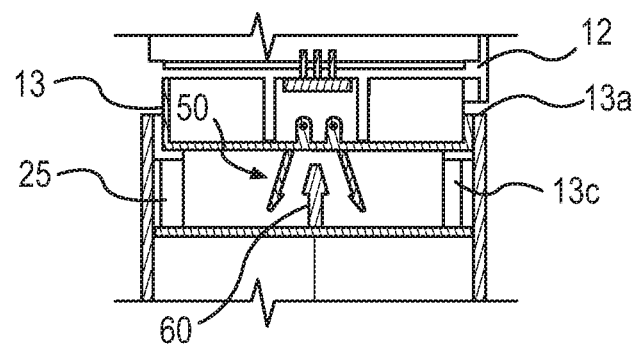

In at least one embodiment, plunger 25 may move along reservoir inner surface 23e by interlocking with carrier 13 (as described in more detail in FIGS. 3A and 3B). In some cases, plunger wall 27a may receive or contain at least the carrier second portion 13b within its lumen. Further, in some cases, plunger wall 27a may further receive at least a portion, or all, of the first portion 13a of carrier 13. In at least one embodiment, a bottom face of the second portion 13b of carrier 13 may abut the base 25b of plunger 25. A top edge of plunger wall 27a may also contact the ledge 13c of carrier 13. In at least one embodiment, base 25b of plunger 25 may include a locking mechanism that engages, e.g., captures, a corresponding lock feature of carrier 13. An exemplary locking mechanism is described in more detail in connection to FIGS. 3A and 3B.

FIGS. 2A-2D show an exemplary drive mechanism 30 that may initiate usage of the negative pressure pump 10. For example, drive mechanism 30 may be used to extend spring 40 (and carrier 13) towards plunger 25. Drive mechanism 30 may be disposed inside drive housing 12. In at least one embodiment, drive mechanism 30 may include an actuator, e.g., button 31, battery (not shown), motor 35, spring 40, gear system 39, and clutch 44. Spring 40 may be comprised of a wound drive spring, constant torque spring, mainspring, or any type of torsion spring.

Figure 2A:
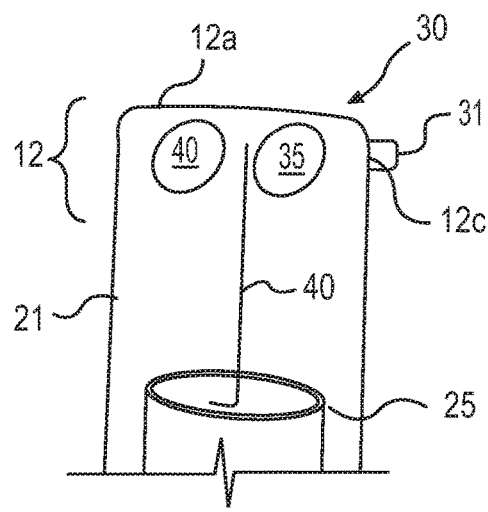
FIGS. 2A-2D provide various views of a mechanical drive mechanism of the reusable drive units of FIG. 1, according to one embodiment of the present disclosure.

As shown in FIG. 2A, drive mechanism 30 may be activated by an actuator, illustrated as button 31. Button 31 may include any nub, protrusion, release, or actuation mechanism extending from the drive housing 12. For example, button 31 may extend from the top of first end 12a or radially outwards from elongate surface 12c. Once button 31 engages drive mechanism 30, drive mechanism 30 may push a drive spring 40 and carrier 13 through the lumen of the reservoir housing 21. It is noted that other types of actuators, such as switches, may be used to engage drive mechanism 30. Once spring 40/carrier 13 receives plunger 25, plunger 25 may connect to spring 40/carrier 13.

Figure 2B:
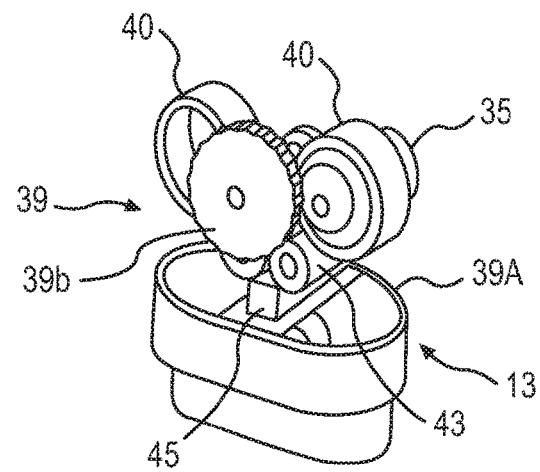
Figure 2C:
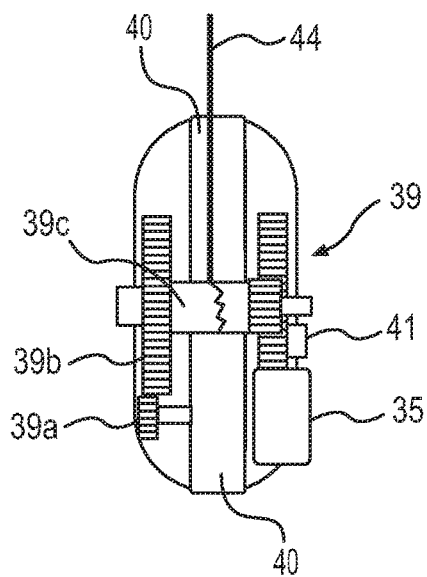
Figure 2D:
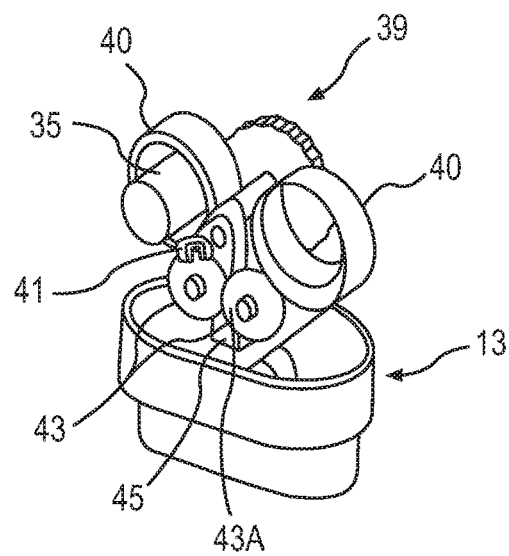

FIGS. 2B-2D provide views of exemplary drive mechanism 30, including motor 35, gear system 39, spring 40, lock gearing 41 (shown in FIGS. 2C and 2D), contact wheels 43, and mount 45. In at least one embodiment, button 31 (of FIG. 2A) may activate motor 35 of drive mechanism 30. Motor 35 may include any type of electrical, battery-operated, single-use, or rechargeable motor. In one embodiment, motor 35 may stop running when carrier 13 contacts or otherwise engages plunger 25. Motor 35 of drive mechanism 30 may cause movement of the gear system 39.

Gear system 39 may include a torque-reducing series of gears that translate power provided by the motor 35 to spring 40. For example, motor 35 may be connected to a gear 39a of gear system 39 (e.g., as shown in FIG. 2B). As shown in FIG. 2C, gear 39a may be adjacent to a second gear, e.g., gear 39b. Motor 35 may move gear 39a, which may then translate motion to a gear 39b. Gear 39b may include gear shaft 39c. Gear shaft 39c may be in contact with spring 40. In at least one embodiment, gear shaft 29c may include teeth or protrusions that may interlock with other gears (e.g., lock gearing 41, as explained in further detail below).

In at least one embodiment, drive mechanism includes two or more springs, which may be wound drive springs and/or constant torque springs. For example, spring 40 may include two wound drive springs. Further, gear shaft 39c may be positioned between the two drive springs (e.g., as shown in FIG. 2C). In at least one embodiment, both of the two wound drive springs of spring 40 may be biased to be retracted in the drive housing 12. Exemplary springs may include constant torque springs. Spring(s) 40 may be retracted and wound inside drive housing 12 while at an exemplary default position. Motor 35 may cause the gear system 39 to unwind the spring 40 and uncoil the spring 40 out against the biased position of spring 40.

In at least one embodiment, gear system 39 may further include lock gearing 41 (e.g., as shown in FIGS. 2C and 2D). In an exemplary configuration, lock gearing 41 may be disposed on one side of spring 40, while gear 39a and gear 39b may be disposed on another side, e.g., an opposite side, of spring 40. Lock gearing 41 may include protrusions that interlock with a corresponding member of gear system 39 (e.g., protrusions of gear shaft 39c as shown in FIG. 2C). The interlocking of lock gearing 41 with gear shaft 39c may provide a one-way clutch 44 (as shown in FIG. 2C), which may stop the motion of gear system 39 in lowering the spring 40 (and carrier 13) into the lumen of the reservoir 20. One-way clutch 44 may be used to disengage motor 35 from spring 40. The clutch 44 may allow connection of an optional external winding handle/key to be used (as an alternative to the motor 35 extending spring 40 to move carrier 13). If the side of the clutch 44 (with gear 41 in FIG. 2C) is turned clockwise, gear 39c may slide axially so that the teeth mating with gear 41 disengage due to the angle of the teeth. A separate clutch/mechanism may be used to disengage motor 35 when the spring(s) 40 retract so the spring(s) 40 do not need to provide torque necessary to drive the motor backwards. Alternatives could include allowing friction wheels to separate or gears to disengage due to spring force, or an additional interface could be added which transmits force only when the motor applies torque to the gears.

In operation, motor 35 may engage gear system 39 to extend spring 40 through reservoir 20 until carrier 13 attaches to plunger 25 (at plunger 25's default position at the bottom of reservoir 20). In particular, contact wheels 43 may be positioned under the gear system 39. Contact wheels 43 may include two circular wheels that contact one or more drive springs 40 that translate motion to springs 40. Alternatively, one or more contact wheels 43 may contact a single spring 40. The contact wheels 43 may be driven by the gear train. Contact wheels 43 may include a high friction, compliant surface (e.g., rubber). The wheels 43 may be spaced such that they pinch the spring(s) 40 between them, advancing the spring(s) 40 by friction as they turn. The wheels 43 may be made of rubber or any non-slip material. In at least one embodiment, contact wheels 43 may further secure the position of spring 40 and maintain friction with spring 40 so that spring 40 is fed into the lumen of reservoir 20, rather than unraveling into the drive unit 11 or gear system 39. For example, if spring 40 includes two springs, each of the springs 40 may feed through a contact point 43a between the two contact wheels 43 (e.g., as shown in FIG. 2D). As an alternate embodiment, spring 40 may be a single spring 40.

In one embodiment, carrier 13 may include a mount 45 (e.g., as shown in FIGS. 2B and 2D). In one embodiment, mount 45 may include a block or protrusion positioned between carrier 13 and the components of drive mechanism 30. In at least one embodiment, mount 45 may secure spring 40 to carrier 13, so that as spring 40 is driven by drive mechanism 30, carrier 13 moves as well.

FIG. 3A shows an exemplary locking mechanism for securing carrier 13 to plunger 25, prior to filling reservoir 20. FIG. 3B shows an exemplary embodiment of disengaging carrier 13 from plunger 25, e.g., once reservoir 20 is filled.

In at least one embodiment, the locking shown in FIG. 3A may take place when the plunger 25 is at the bottom of reservoir 20 (e.g., when plunger base 27b lies against the base at reservoir second end 23b). In at least one embodiment, carrier 13 may be lowered through the lumen of reservoir 20 (using drive mechanism 30 and spring 40), until carrier 13 contacts plunger 25. Spring 40 may be fastened to carrier 13 using mount 45. In the embodiment of FIG. 3A, spring 40 may connect permanently, in any suitable fashion, to carrier 13. This connection may involve a separate component or features integral to the spring 40 and carrier 13 which connect. In one embodiment, mount 45 may include a portion 45a that is secured to spring 40, as well as a portion 45b that extends into and connects to at least a portion of the carrier first portion 13a. As previously described, at least a portion of carrier 13 may be received inside a cavity of plunger 25, and a surface (e.g., a rim or ledge) of carrier 13 may contact an outer surface of plunger 25. In at least one embodiment, carrier 13 may include one or more pivoting barbs 50. In at least one embodiment, barbs 50 may extend from the first portion 13a of carrier 13 to the second portion 13b of carrier 13. Barbs 50 may include two barbs 50, each of the two barbs 50 including a rounded head 53 at one end and a hook 55 at the opposite end. The rounded head 53 may be biased towards a closed position where each of the hooks 55 substantially points radially inward towards the plunger base 27b.

In at least one embodiment, plunger 25 may include an interlocking member 60. Interlocking member 60 may include at least two surfaces that correspond to and engage one or more surfaces of hooks 55. Carrier 13 may engage plunger 25 when barbs 50 of carrier 13 lock against interlocking member 60 of plunger 25.

Figure 3C:
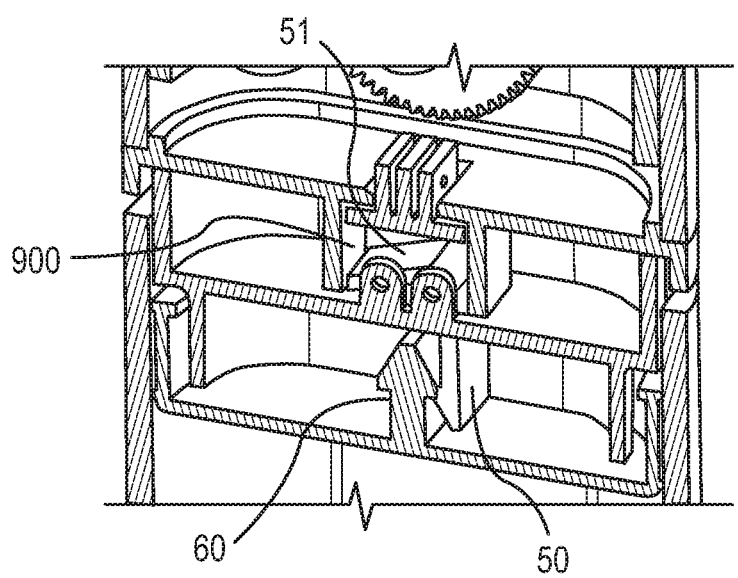

FIG. 3B shows carrier 13 releasing plunger 25. The action of FIG. 3B may occur once spring 40 is fully retracted and the carrier first portion 13a is in contact with second end 12b of drive housing 12. In at least one embodiment, the contact between the carrier 13 and drive housing 12 may cause barbs 50 to rotate and release interlocking member 60. In some embodiments, barbs 50 may release interlocking member 60 upon activation by a user (e.g., pressing a release button or other actuator). FIG. 3C shows a cross section including one of the barbs 50. Barbs 50 may be spring loaded (spring not shown) towards the center axis of pump 10 and reservoir 20 to capture the interlocking member 60 on the plunger 25. When the carrier 13 (pulled by spring 40) reaches the end of its travel, protrusions 900 on the drive housing 12 contact an arm 51 of each of the barbs 50 and pivot them so they disengage from the interlocking member 60. Alternate locking mechanisms may include any configuration of magnets, latches, catches, fastenings, interlocking members, snaps, etc.

Figure 4C:
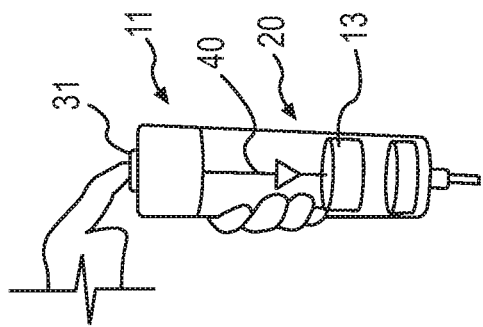
FIGS. 4A-4G provide an exemplary method of using an exemplary negative pressure pump comprised of a reusable drive unit and a disposable reservoir, according to one embodiment of the present disclosure.
Figure 4D:
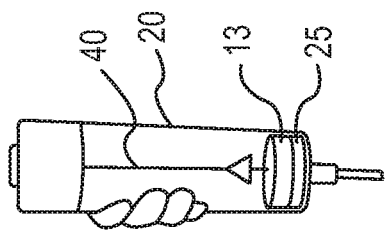
Figure 4B:
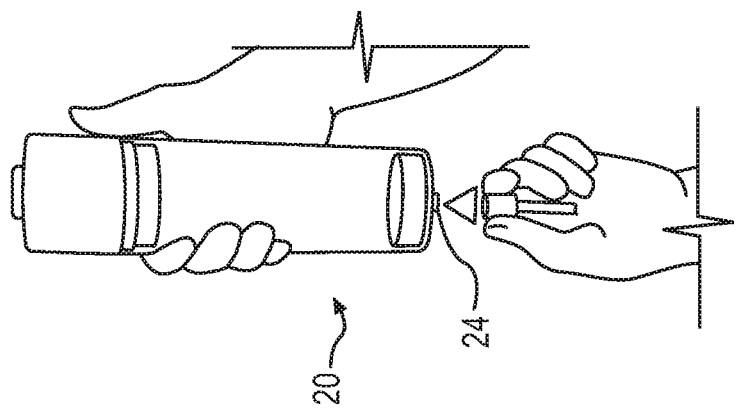
Figure 4A:
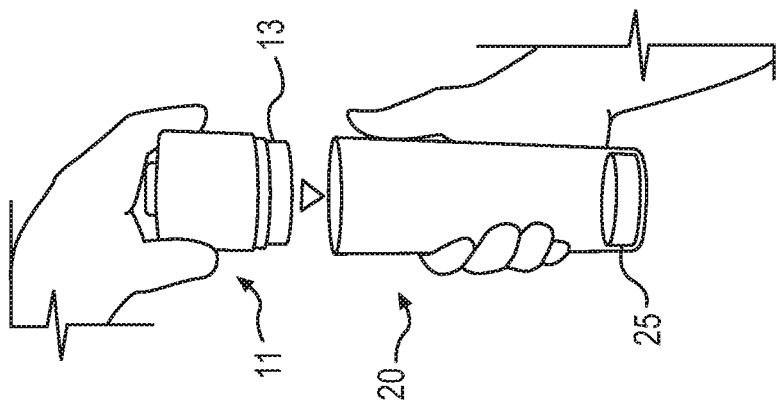

FIGS. 4A-4D illustrate an exemplary method of preparing the negative pressure pump 10 for use. First, reusable drive unit 11 may be secured to reservoir 20. As shown in FIG. 4A, at their initial positions, carrier 13 may be at the base of reusable drive unit 11 and plunger 25 may at the base of reservoir 20. FIG. 4B depicts a step of securing a tube to manifold connector 24 at the base of reservoir 20. (This step may occur at any point prior to the steps of FIGS. 4E-4G.) An opposite end of the tube may be in fluid communication with a target site, such as an internal or external wound of a patient, including prior to the step shown in FIG. 4A.

FIG. 4C shows a step in which interaction with button 31 may activate a motor 35 (see FIGS. 2A-2D) in the reusable drive unit 11. The reusable drive unit 11 may prompt spring 40 to extend from reusable drive unit 11, into reservoir 20. For example, the motor 35 may cause spring 40 to unwind from drive housing 12. Drive unit 11 may include a carrier 13 attached to the end of a spring 40. As drive unit 11 lowers spring 40 into reservoir 20, the movement of spring 40 may also push carrier 13 towards the base of reservoir 20.

FIG. 4D illustrates an exemplary step where spring 40 may be extended through the length of the lumen of reservoir 20, and carrier 13 may contact plunger 25. At this step, carrier 13 may lock with plunger 25. In at least one embodiment, carrier 13 may automatically attach to the plunger 25 upon contact. For example, carrier 13 may attach to plunger 25 by engaging a molded barb feature (e.g., as depicted in FIG. 3A).

Figure 4G:
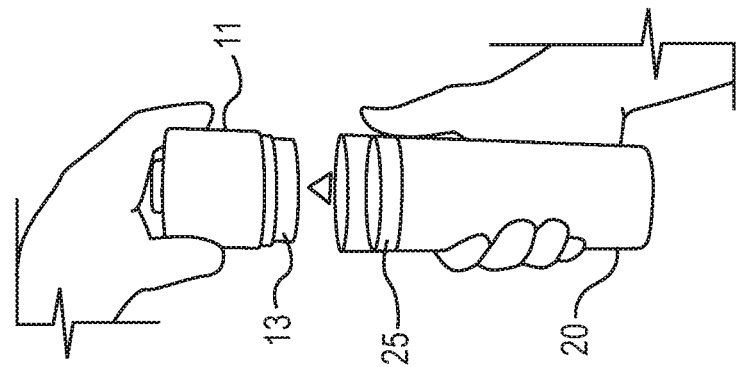
Figure 4F:
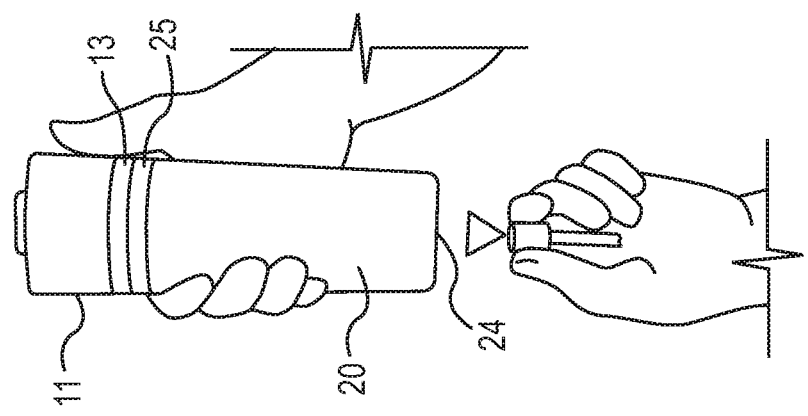
Figure 4E:
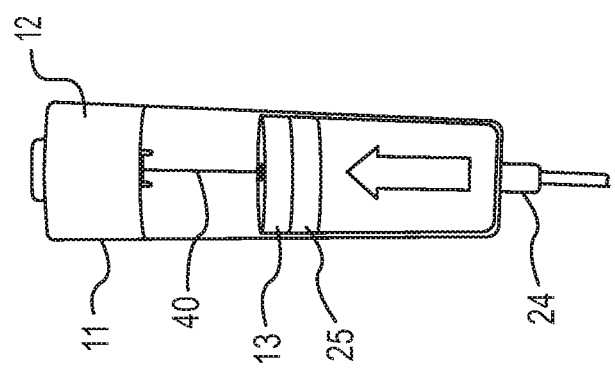

FIGS. 4E-4G show an exemplary embodiment of using negative pressure pump 10. For example, the motor 35/drive mechanism 30 (see FIGS. 2A-2D) may disengage (e.g., turn off) once carrier 13 contacts and locks with plunger 25. In at least one embodiment, spring 40 may be biased to retract inside drive housing 12. When the negative pressure pump 10 is in use (and drive mechanism 30 is turned off), spring 40 may automatically return to its retracted position inside drive housing 12. This motion of plunger 25 may generate negative pressure inside the lumen of reservoir 20.

FIG. 4E depicts a step of using a spring powered mechanism for moving a plunger to generate negative pressure, e.g., constant negative pressure, to draw fluid into a reservoir. In particular, FIG. 4E depicts an exemplary step in which spring 40 may automatically retract, towards and into drive unit 11. Since spring 40 may be connected to plunger 25 (by way of carrier 13), the upwards motion of spring 40 may also pull plunger 25 upwards through the reservoir lumen. This negative pressure may cause fluid to be drawn from the connected tubing, into reservoir 20. In other words, fluids from a tube (fastened to manifold connector 24) may flow into the lumen of reservoir 20 as the carrier 13 and plunger 25 travel up through the reservoir lumen. Such fluids may comprise body fluids from a target site of a patient, e.g., an internal or external wound or other location of a patient, wherein collection and removal of fluid may be desired.

Once the reservoir is full, the tube optionally may be unfastened from manifold connector 24 (e.g., as shown in FIG. 4F). The drive unit 11 optionally may also be disconnected from reservoir 20. In at least one embodiment, plunger 25 may stay in the reservoir 20 to provide a seal (via an O-ring between plunger 25 and reservoir wall 23c, for example) and prevent the reservoir contents from spilling. For example, removing reservoir 20 from drive unit 11 may involve disengaging the carrier 13 from plunger 25 (e.g., as shown in FIG. 4G). The step illustrated in FIG. 4G may include unlocking mechanisms illustrated in FIG. 3B, or any other form of releasing plunger 25 from carrier 13, including an automatic disengagement at the top of the stroke of plunger 25. Reservoir 20 may be discarded, e.g., the used reservoir 20 being disposable, while drive unit 11 may be reused with another reservoir 20. Manifold 24 may include a one-way valve so that contents of reservoir 20 are sealed in reservoir 20. In some embodiments, drive unit 11 does not contact bodily fluids, and therefore does not require cleaning.

In summary, once a reservoir is filled, the plunger may seal the full reservoir so that the reservoir may be removed from the reusable drive unit. In at least one embodiment, the reusable drive unit may automatically disconnect from the plunger (e.g., as shown in the example of FIG. 3B). In some embodiments, the reusable drive unit and plunger may be joined in a connection, and a user may unlock the connection to release the reservoir from the drive unit. In at least one scenario, releasing the plunger from the drive unit may involve the carrier disengaging the plunger. In at least one case, the carrier may automatically release the plunger and the plunger may seal the reservoir. A user may then manually remove the drive unit (and carrier) from the reservoir (and plunger). For example, a latch may hold the drive unit to the reservoir, or the drive unit may engage the reservoir via a friction fit. A user may disconnect the drive unit from the reservoir once the internal components of the drive unit and reservoir (e.g., the carrier and plunger, respectively) are disengaged.

In at least one embodiment, a new, empty reservoir may be attached to the drive unit (e.g., reusable drive unit) once the reservoir filled with collected fluid is removed/released from the drive unit. The process may then restart (e.g., with the steps of FIGS. 4A-4D and a new reservoir/plunger), where a user may engage an actuator, e.g., press a button, to activate the motor drive mechanism to lower the spring into the lumen of the new reservoir. The carrier may attach to the plunger of the new reservoir and allow fluid to fill the new reservoir. In short, a full reservoir may be detached from the reusable drive unit, a new empty reservoir may be secured to the reusable drive unit, a user may reset the spring to initiate usage of the new reservoir, and collection of fluid can continue. In embodiments therefore, a system, or kit, may include a single reusable drive and a plurality of disposable reservoirs, and optionally tubing and/or a tubing manifold. The system or kit may include a charger for charging a power supply of the drive unit, such as a rechargeable battery.

Figure 5:
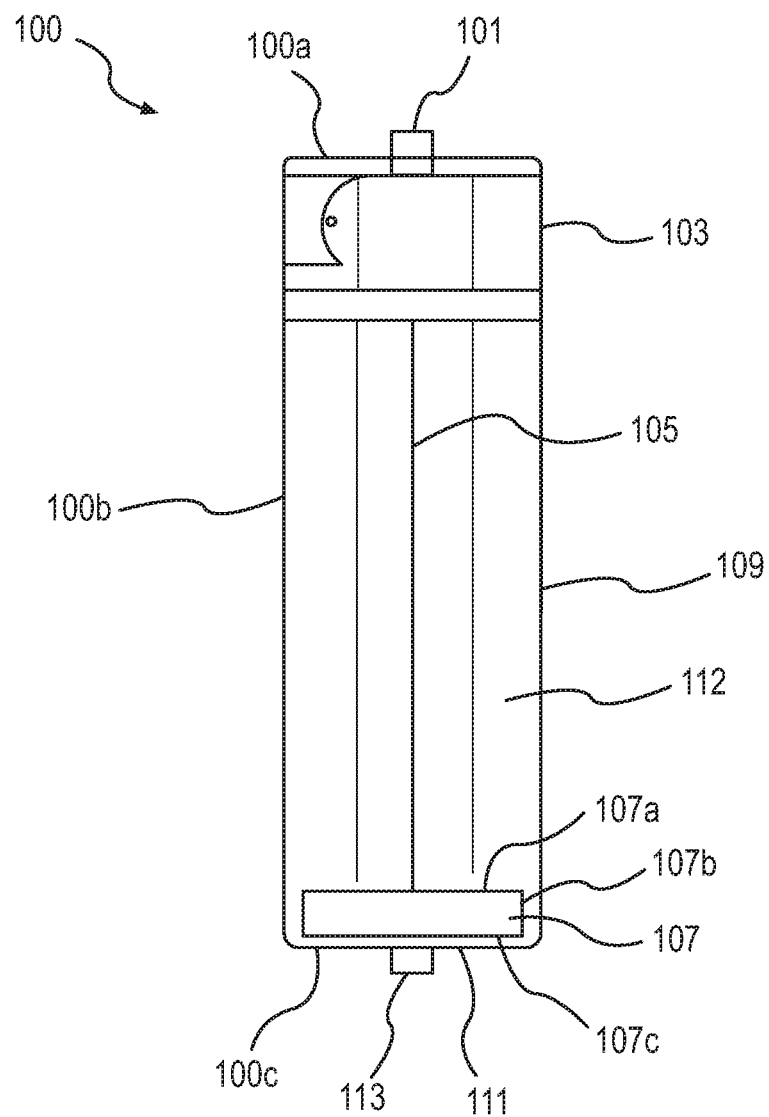
FIG. 5 provides a view of an exemplary disposable negative pressure pump, according to a second embodiment of the present disclosure.

FIG. 5 depicts a second exemplary embodiment of a negative pressure pump 100. In particular, the example shown in FIG. 5 may be intended for single use, e.g., fully disposable. Disposable negative pressure pump 100 comprise material or materials suitable for single-use, including, but not limited to, plastic, glass, metal, silicone, or a combination thereof. At least a portion of negative pressure pump 100 may be opaque, transparent, or translucent. Negative pressure pump 100 may be of any suitable cross-sectional configuration, including, but not limited to, rectangular, circular, elliptical, triangular, or oval.

In at least one embodiment, negative pressure pump 100 may include a first end 100*a*, a wall 100*b*, and a second end 100*c*. The first end 100*a* may be a solid form of the cross-section of negative pressure pump 100. For example, if negative pressure pump 100 comprises a plastic structure with an elliptical cross-section, first end 100*a* may be a plastic ellipses. In at least one embodiment, first end 100*a* may include an opening for activation button 101. The activation button 101 may be in any shape that may extend from first end 100*a*. For example, activation button 101 may be a protrusion, a latch, a switch, or any combination thereof.

In at least one embodiment, wall 100*b* may have an outer surface and an inner surface. In at least one embodiment, the outer surface of wall 100*b* may include markings or other indicators, for instance, indicating volume. The outer surface of wall 100*b* may further include anti-slip coatings, ridges, protrusions, adhesives, or a combination thereof for ease of handling. In at least one embodiment, the inner surface of wall 100*b* may form a lumen 112. Drive housing 103, spring 105, and plunger 107 may all be contained inside lumen 112. At least a portion of lumen 112 may serve as reservoir 109. In one embodiment, the inner (or lumen) surface of wall 100*b* may be smooth.

In at least one embodiment, drive housing 103 may be disposed adjacent the first end 100*a*, at a top portion of lumen 112. Drive housing 103 may contain a drive mechanism that is activated by activation button 101. Drive housing 103 may comprise any material or materials suitable for single-use, including, but not limited to, plastic, glass, metal, silicone, or a combination thereof. The drive housing 103 and a drive mechanism contained therein are described in more detail in connection to FIGS. 6A-7C.

Spring 105 may include any suitable type of spring, e.g., a coil spring, torsion spring, clock spring, etc. In the device of FIG. 5, spring 105 may be biased to retract into drive housing 103. In some embodiments, spring 105 may include a wire or cable that does not store energy. In at least one embodiment, spring 105 may retract into the drive housing 103 upon actuation of the activation button 101. One end of spring 105 may be secured inside drive housing 103, and another end of spring 105 may be attached to or otherwise coupled to plunger 107. At a default position prior to the use of negative pressure pump 100, plunger 107 may lie at second end 100*c* of negative pressure pump 100. This may mean that, at a default position, spring 105 may extend through the length of lumen 112, e.g., spring 105 may stretch from drive housing 103 (adjacent first end 100*a*) to plunger 107 (at the second end 100*c*). Spring 105 may include one or more springs and/or a cable attached to a member of the drive mechanism. In at least one embodiment, spring 105 may include a spring portion and a cable or wire portion.

In at least one embodiment, plunger 107 may have substantially the same cross-section as lumen 112. Plunger 107 may include a top 107*a*, a side wall 107*b*, and a bottom 107*c*. In at least one embodiment, top 107*a* may be fixedly attached to spring 105. Plunger side wall 107*b* may be flush against the inner surface of wall 100*b*. For example, plunger side wall 107*b* may directly contact the inner surface of wall 100*b*, or a seal, such as an O-ring, may be between, and directly contact each of, wall 100*b* and the inner surface of wall 100*b*. Plunger bottom 107*c* may be positioned at the pump second end 110*c* when the negative pressure pump 100 is at a default position. When the negative pressure pump 100 is in use, plunger 107 may move along lumen 112 (e.g., plunger 107 being slidable along the inner surface of wall 100*b*), towards the drive housing 103.

In one embodiment, pump second end 100*c* may include a base 111 and manifold connector 113. In at least one embodiment, base 111 may close the lumen formed by pump wall 100*c*. In at least one embodiment, the default position of plunger bottom 107*c* may be inside lumen 112 and adjacent to, e.g., on top of, base 111. Base 111 may include an opening comprising manifold connector 113. The opening may provide access to the lumen formed by wall 100*b*. Manifold connector 113 may include a valve, e.g., a one-way valve, that may be attached to tubing that extends to the target site, e.g., on or within a patient's body, permitting fluid to enter reservoir 109 but preventing fluid from escaping reservoir 109.

Figure 6A:
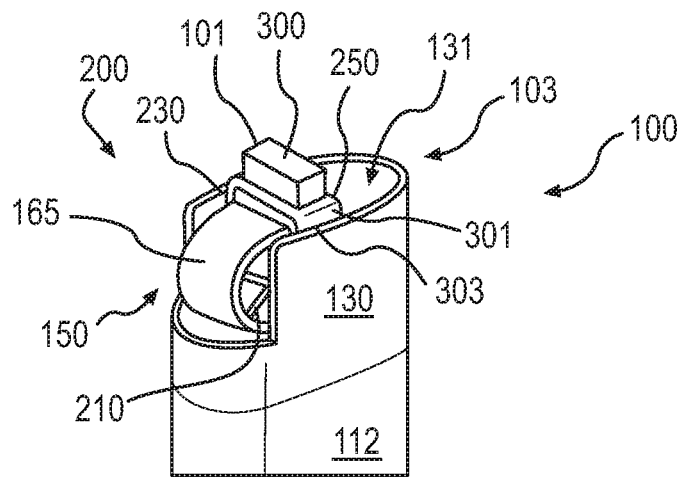
FIGS. 6A-6C provide various views of a mechanical drive assembly of a disposable negative pressure pump, according to the second embodiment of the present disclosure.
Figure 6B:
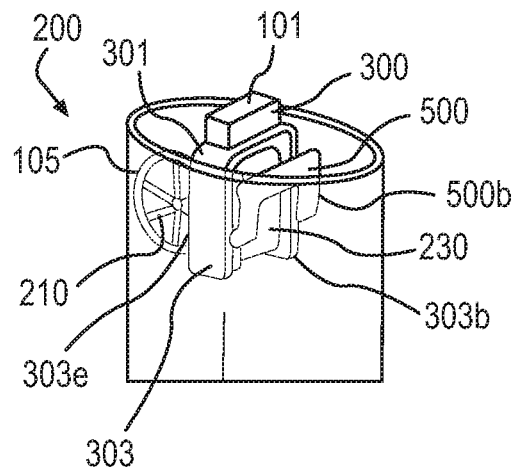
Figure 6C:
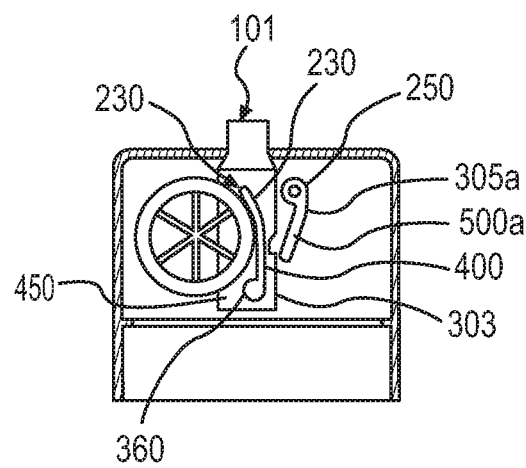

FIGS. 6A-6C include various views of drive housing 103 and an exemplary drive assembly 200. Because pump 100 may be built for one-time use and disposable, drive assembly 200 of pump 100 may include fewer components and/or employ a different mechanism than the drive mechanism 30 of reusable drive unit 11. Further, for example, drive assembly 200 may release and store a spring (as described further herein), whereas drive mechanism 30 may actively move a spring against its biased position. FIGS. 6A-6C describe an exemplary drive assembly 200 and related components in more detail.

As shown in FIG. 6A, drive housing 103 may include a wall 130. In at least one embodiment, wall 130 may have a cross-section that corresponds to lumen 112. Wall 130 may define its own lumen 131. In at least one embodiment, wall 130 may include a cutout 150. Cutout 150 may include a portion of wall 130 that is at a different height from another portion of wall 130. Cutout 150 may be of any appropriate shape or size. In at least one embodiment, cutout 150 may provide access to the drive assembly 200. For example, drive assembly 200 may be positioned inside lumen 131. A wall 130 that is the same height for the entire perimeter of lumen 131 may block access to drive assembly 200. Cutout 150 may expose at least a portion of drive assembly 200.

As shown in FIGS. 6A-6C, drive assembly 200 may include activation button 101, spring 105, hub 210, wedge 230, and latch 250. FIGS. 6B and 6C, in particular, show exemplary configurations of activation button 101, wedge 230, and latch 250. In at least one embodiment, activation button 101 may include a protrusion 300, mount 301, and arms 303 (e.g., as shown in FIGS. 6A and 6B). The activation button arms 303 may further include notches 305 (shown in FIG. 6C and explained in more detail below). In at least one embodiment, protrusion 300 may be a portion of activation button 101 that extends from the top of pump 100. A user may activate pump 100 by pushing protrusion 300. Protrusion 300 may be of any shape, including but not limited to rectangular (as shown in FIGS. 6A-6C), circular, square, star-shaped, or elliptical, etc. Protrusion 300 optionally may include grooves or anti-slip surface(s) to facilitate handling.

In at least one embodiment, protrusion 300 may be disposed on top of mount 301. Mount 301 may include a surface that joins protrusion 300 to arms 303. In at least one embodiment, arms 303 may extend on either side of spring 105. For example as shown in FIG. 6B, spring 105 may be disposed between arm 303a and arm 303b ("arms 303"). In at least one embodiment, arms 303 may also fit over wedge 230 and hold wedge 230 against spring 105 (while at a default position before usage of pump 100). In at least one embodiment, each of arms 303 may include a notch 305 at one side. For example, FIG. 6C shows arm 303a with a notch 305a. Latch 250 may be positioned at the same side as the notches 305 of arms 303.

In at least one embodiment, spring 105 may comprise a wound drive spring disposed on hub 210. Spring 105 may unwind and/or wind onto hub 210. In at least one embodiment, hub 210 may include a wheel, a casing, a rubber roller, or any component that can capture spring 105 so that spring 105 remains untangled. Hub 210 may be secured via an axle extending across the pump 100 (as shown in FIG. 6C), so that hub 210 rotates about the axle.

In at least one embodiment, wedge 230 may comprise a pivotable arm 400 with a stopper 450 disposed at one end of the arm 400. At a default position, stopper 450 may be held against spring 105 by arms 303 of activation button 101 (e.g., as shown in FIGS. 6C and 7A).

Latch 250 may include bar 500, which joins locking arm 500a to locking arm 500b ("locking arms 500"), as shown in FIG. 6B. In at least one embodiment, bar 500 may be positioned alongside arms 303 of activation button 101. Bar 500 may hold locking arms 500 adjacent to notches 305 (as shown in FIG. 6C). In at least one embodiment, at least a portion of each of the locking arms 500 may extend into at least a portion of each of the notches 305. For example, locking arm 500a may fit into notch 305a. FIGS. 7A-7C illustrate the interaction of locking arms 500 with notches 305 in more detail.

FIGS. 7A-7C depict exemplary operation of drive assembly 200. At one exemplary default position shown in FIG. 7A, activation button 101 is not depressed. Protrusion 300 may extend fully upward from the first end 100a of pump 100 and the internal components of drive assembly 200 may be at rest (e.g., not in motion) including spring 105 fully extended to a bottom of reservoir 109. In at least one embodiment, stopper 450 of wedge 230 may abut spring 105. Hub 210 and spring 105 therefore are fixed and stationary. Further, locking arms 500 of latch 250 may each abut a surface of activation button arms 303, below and adjacent to notches 305 (see FIG. 6C).

Upon depression of activation button 101 (as shown in FIG. 7B), protrusion 300 may extend into the first end 100a of pump 100. Mount 301 (see FIGS. 6A and 6B) may translate the downward motion to arms 303. Because wedge 230 may be coupled to arms 303, the downward motion of arms 303 may force a downward motion of stopper 450 (and/or) a pivoting of elongate arm 400. The motion of wedge 230 may release spring 105, and spring 105 may begin to wind onto hub 210. In other words, depression of the button 101 may release spring 105, which may cause spring 105 to retract onto hub 210 due to its bias to retract.

By completing a stroke of protrusion 300, arms 303 may lower sufficiently to allow locking arms 500 to pivot and enter their corresponding notches 305 (as shown in FIG. 7C). Latch 250 may permanently catch the activation button 101 and wedge 230.

FIGS. 8A-8D illustrate an exemplary method of using the negative pressure pump 100, where the entire pump device may be single-use. Pump 100 may include a spring-powered negative pressure drive assembly 200 with an attached fluid reservoir 109. In particular, pump 100 may include an extended spring 105 attached to a plunger 107 positioned at the bottom of reservoir 109 (e.g., as shown in FIG. 8A). One end of a tube may be connected to manifold connection 113, with the other tube end in fluid communication with a wound cavity, or other portion of a patient's body or target site, requiring fluid collection. Pressing a button (e.g., activation button 101) may release a wedge stopper in the drive assembly 200 (not shown). The spring may be charged to store energy prior to usage (e.g., during manufacturing). Accordingly, the release of the wedge stopper may cause the spring 105 to retract (e.g., as shown in FIG. 8B). Since spring 105 is connected to plunger 107, the winding of spring 105 may pull plunger 107 through reservoir lumen 112 and generate negative pressure in the reservoir 109. In at least one embodiment, one end of spring 105 may be connected to plunger 107. In some embodiments, spring 105 may be coupled to, e.g., attached to, the plunger 107 via a cable, so that release of the spring 105 pulls a cable, and pulling of the cable attached to plunger 107 generates negative pressure in reservoir 109. The negative pressure in reservoir 109 may permit reservoir 109 to draw and collect fluid from the target site, e.g., of a patient (e.g., as shown in FIG. 8C). When the reservoir 109 is full and/or the desired amount of fluid drawn into the reservoir 109, the tubing optionally may be disconnected from manifold connection 113 (e.g., as shown in FIG. 8D). The entire device (pump 100) may then be discarded.

Figure 9A:
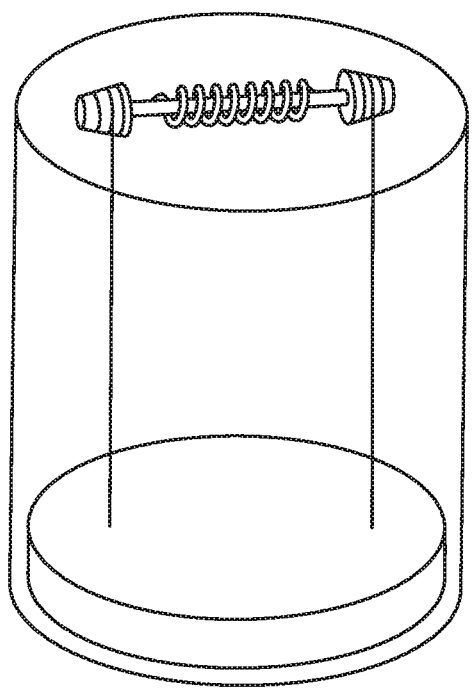
FIGS. 9A-9B, 10A-10C, 11A-11B, and 12 show various alternative embodiments of a drive assembly of a negative pressure pump, according to embodiments of the present disclosure.
Figure 9B:
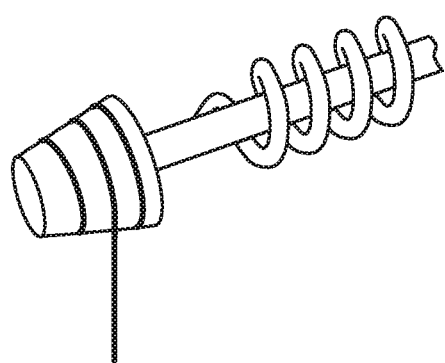

FIGS. 9A and 9B show another exemplary device that includes a torsion spring. The torque produced by a torsion spring may increase as the spring is wound and decrease as it is unwound. However, a substantially constant force (and substantially constant negative pressure) on the piston may be desired. The tension in a wire or other type of cable may be calculated as the spring torque divided by the radius of the sheave. The wire may be captured in the grooves in the sheaves. As the spring unwinds and torque decreases, the radius of the sheave where the wire leaves the sheave may decrease. A constant force can be maintained if the ratio of spring torque to sheave diameter (where the wire exits) is maintained.

Figure 10C:
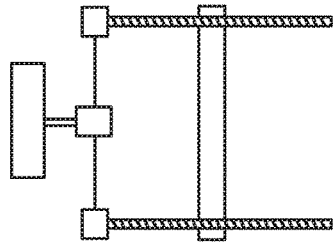
Figure 10B:
Figure 10A:
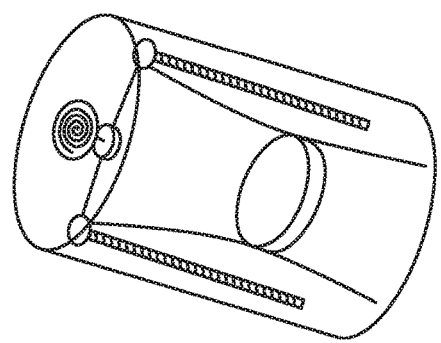

FIGS. 10A-10B show arrangements using principles similar to FIGS. 9A and 9B. Again, the figures are not exhaustive as to the mechanisms involved in how the springs may be wound or released. The figures show methods to achieve constant force from clock springs (e.g., a wound multicore ribbon cable), which may provide oscillating or fluctuating torque. FIGS. 10A-10C show two pulleys attached to the clock spring so that the pulleys may spin as the clock spring unwinds. A drive belt may be wrapped around the pulleys and each of two pulleys attached to variable pitch lead screws, so that the torque and motion of the clock spring may be transmitted to the two lead screws. Wires may be connected from the nuts on the lead screws to the piston, so that the force on the nuts may be applied to the piston, creating negative pressure. The force on the nuts may be proportional to the torque on the screws divided by the screw lead, and the torque on the screws may be proportional to the torque in the spring. Therefore, even in cases in which the spring torque is not constant, a constant or substantially constant force can be maintained if the ratio of the spring torque to screw lead is constant.

Figure 11B:
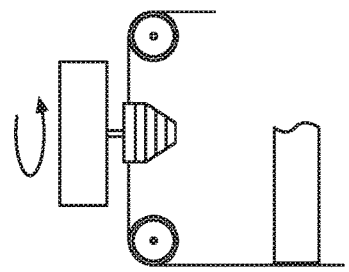
Figure 11A:
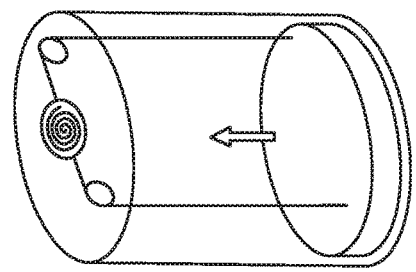

FIGS. 11A and 11B may be similar in concept to the embodiments of FIGS. 9A and 9B, except a clock spring may be used in place of the wire torsion spring (e.g., a helical spring), and two wires may be wrapped on the same tapered sheave. A constant force can be maintained if the ratio of spring torque to sheave diameter (where the wire exits) is maintained.

Figure 12:
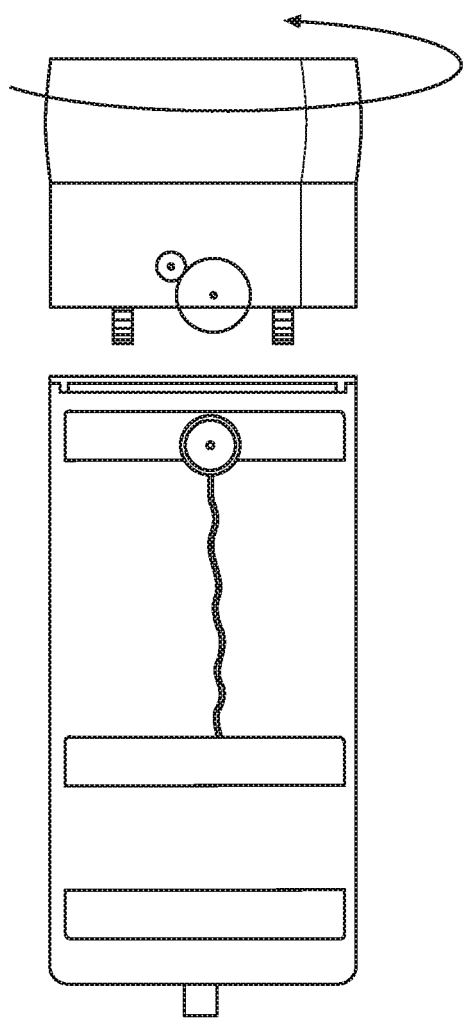

FIG. 12 shows an arrangement where a "knob" on the top of the device could be twisted to energize a spring or cable in the gear drive. In this concept, the plunger may start at the bottom of the reservoir, and a cable attached to the plunger may be wrapped around a pulley at the top of the reservoir. For example, the cable may be attached or fixed to a cable attachment on the pulley. As the knob is wound, the cable may wrap around the pulley. (In at least one embodiment, the cable is nearly straight rather than slack.) In this configuration, the gear drive can be separated from the reservoir. Engaging the gear drive with the pulley may wind up the cable and move the plunger.

FIGS. 13A-13F show an exemplary pressure-actuated negative pressure pump, according to some embodiments of the present disclosure. In at least one embodiment, for every 1 mL of fluid, 260 mL of vapor may be generated resulting in a potential collected fluid volume of 260 mL. The fluid can be a single fluid or a mixture of different fluids that have a vapor pressure that is at or proximate atmospheric pressure (760 mmHg) plus the desired device vacuum pressure (e.g., 125 mmHg) plus mechanical losses in the system (e.g., 700 mmHg). Thus, an approximate 1585 mmHg vapor pressure may be used at 20° C. An exemplary fluid mixture that can produce this vapor pressure is n-pentane and n-butane. Many other fluids and fluid mixtures are possible too.

In at least one embodiment, 1 mL of the n-pentane/n-butane mixture may be placed in the positive pressure compartment 1550 of the device during manufacturing. The plunger 1560 of this compartment may be locked into place until user activation of the device. The device may be designed to handle the pressure of the mixture during the storage period, much like a hand-held cigarette lighter. At activation, the plunger 1560 in the positive pressure compartment 1550 may be pushed, increasing the volume of that compartment, and also increasing the volume of the negative pressure compartment 1555, thus creating the desired vacuum pressure. The fluid mixture may increase in volume, e.g., 260 times (1 mL to 260 mL) as it transitions from a liquid to a vapor, all while maintaining the same vapor pressure. In such embodiments of a 250 mL reservoir vacuum device, less than 1 mL of fluid could be used to actuate the device. The device 1600 of FIGS. 13A-13F may include two compartments (one positive pressure 1550, and one negative pressure 1555) each with a plunger 1560 connected by a rigid structure. The positive pressure compartment 1550 may contain a mixture of fluids that generate a vapor pressure causing positive pressure. The plunger 1560 may initially be locked in position at the bottom of the reservoir, as shown by FIG. 13E. When the locking mechanism is released, the plunger 1560 moves, thus generating negative pressure in the negative pressure compartment 1555. The plunger 1560 may move through the pressure compartments 1550 and 1555, to a final position as shown in FIG. 13F. Slot 1603 on device top 1601 may be a vent to atmospheric pressure. This entire device 1600 may be a disposable or reusable device.

Figure 14A:
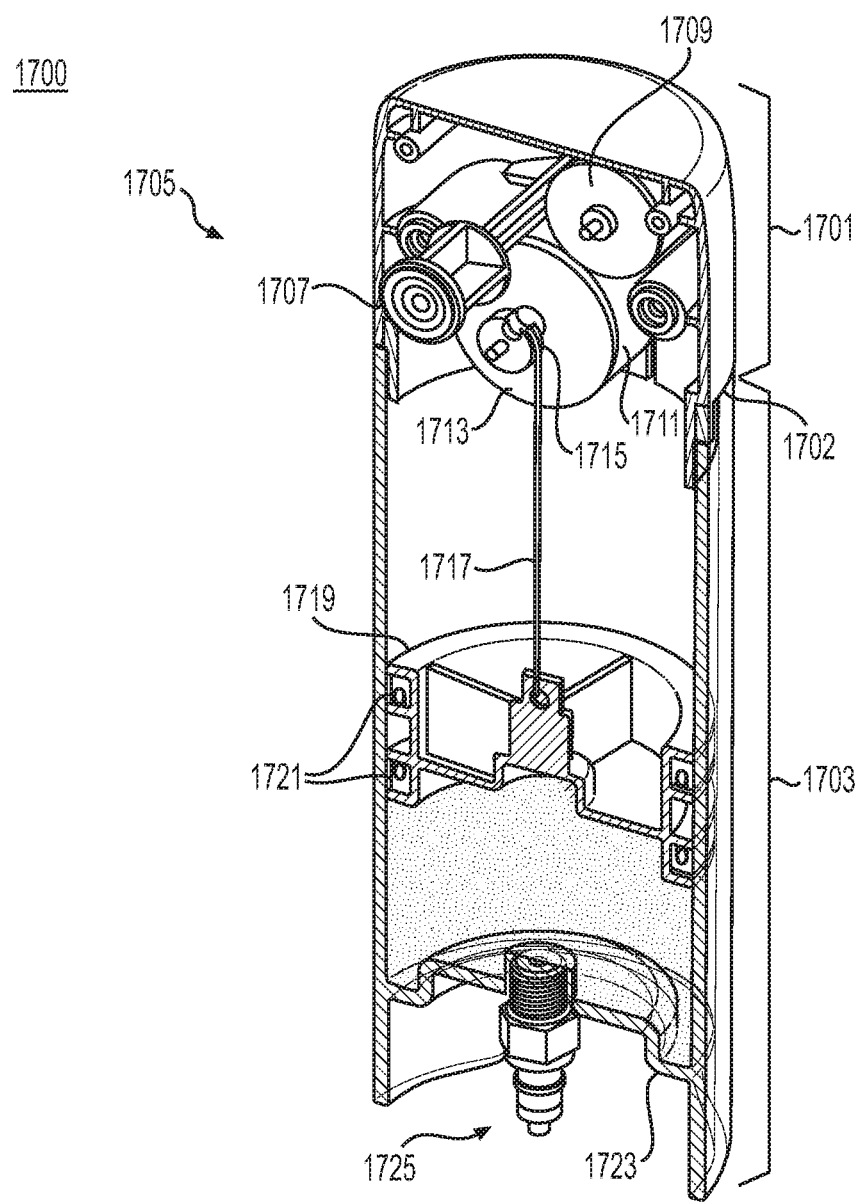
FIGS. 14A and 14B provide cross-sectional, perspective views of exemplary constant torque spring driven negative pressure pumps, according to one embodiment of the present disclosure.
Figure 14B:
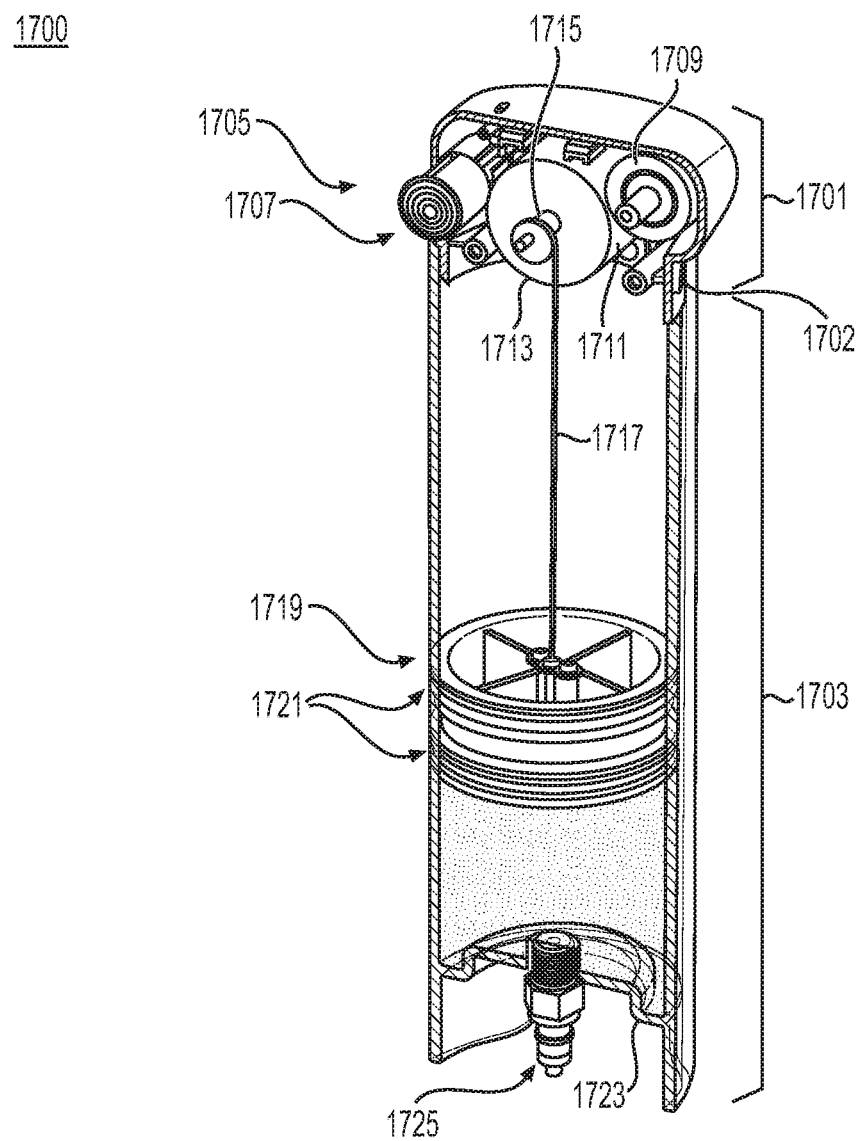

FIGS. 14A and 14B show embodiments of another exemplary negative pressure pump 1700 that includes a torque spring. Negative pressure pump 1700 may be of any suitable cross-sectional configuration, including, but not limited to, rectangular, circular, elliptical, triangular, or oval. Negative pressure pump 1700 may comprise any suitable material or materials, including, but not limited to, glass, plastic, metal, rubber, silicone, or a combination thereof. At least a portion of negative pressure pump 1700 may be opaque, transparent, or translucent.

Negative pressure pump 1700 may include a drive assembly housing 1701 and a reservoir 1703. Housing 1701 and reservoir 1703 may be joined at an interface 1702. Interface 1702 may include an overlap in a portion of housing 1701 and a portion of reservoir 1703, as shown in FIGS. 14A and 14B. For example, the portion of housing 1701 may be configured to fit inside and against an inner surface of the portion of reservoir 1703. As an alternate embodiment, a portion of reservoir 1703 may be configured to fit inside and against an inner surface of housing 1701. The concentric circumferences of housing 1701 and reservoir 1703 may form interface 1702.

In at least one embodiment, housing 1701 and reservoir 1703 may be fixedly coupled so that interface 1702 is permanent. For example, housing 1701 and reservoir 1703 may be adhered together at interface 1702 via glue, other adhesive, or another method of permanent fixation. In some embodiments, pump 1700 may comprise one single integrated unit. In such a case, housing 1701 and reservoir 1703 may be formed during manufacturing as a single integral unit (e.g., from one material), rather than formed from the joining together of housing reservoir 1701 and reservoir 1703. In some embodiments, housing 1701 and reservoir 1703 may be removably coupled so that housing 1701 may be released or separated from reservoir 1703 at interface 1702. For example, housing 1701 and reservoir 1703 may be connected at interface 1702 via a snap-fit, friction-fit, or other releasable engagement. In such a case, housing 1701 may be released from reservoir 1703 (e.g., after reservoir 1703 is full). Then, housing 1701 may be coupled to a second reservoir and reused.

The drive assembly housing 1701 may include a drive assembly 1705. The drive assembly 1705 may be activated by an actuator, e.g., button 1707, having a lock mechanism (shown in more detail at FIGS. 14E and 14F). The drive assembly 1705 may include a spring storage drum 1709, a spring 1711, e.g., constant torque spring, and an output drum 1713 having a cable attachment point 1715. In at least one embodiment, button 1707 may releasably lock the output drum 1713 and storage drum 1709 in a fixed position. Spring storage drum 1709 and output drum 1713 may each comprise cylindrical storage units configured and sized to contain spring 1711. Spring 1711 may have a flat or ribbon-like structure and be made from metal, alloys, plastic, elastomers, electroactive polymers, etc., or a combination thereof. Spring 1711 may be made of a flexible material and have a thickness that allows it to unwind from output drum 1713 and onto spring storage drum 1709. Spring 1711 may be contained on the output drum 1713 while in a default position, during manufacturing. Also during manufacturing, spring 1711 may be biased and energized by winding the spring 1711 onto the output drum 1713. During use, spring 1711 may wind from the output drum 1713 onto the storage drum 1709 when the drums are released from their fixed position via button 1707.

The drive assembly 1705 may drive the motion of a piston. For example the cable attachment point 1715 of output drum 1713 may be a connection point for cable 1717. Cable 1717 may be any suitable flexible elongate member. For example, cable 1717 may comprise a wire, rope, cord, string, etc. Cable 1717 may extend through reservoir 1703 while at a default position. One end of cable 1717 may be attached to the cable attachment point 1715 and the second end of cable 1717 may be connected to a piston 1719. Piston 1719 may form a seal against an inner surface of reservoir 1703, e.g., via O-rings 1721 as shown in FIGS. 14A and 14B, or other suitable annular seal. Piston 1719 may have a default position at the base 1723 of reservoir 1703. For example, a bottom surface of piston 1719 may be in contact with a surface of base 1723 when piston 1719 is at its default position. Accordingly, at a default position from manufacturing, cable 1717 may extend through reservoir 1703: one end of cable 1717 may be connected to the output drum 1713 at the drive assembly 1705 and the other end may be connected to piston 1719 at the base 1723 of reservoir 1703. During pump usage, rotation of the output drum 1713 may cause cable 1717 to wind onto an axle of output drum 1713 and draw piston 1719 through the length of reservoir 1703. In other words, cable 1717 may retract and cause piston 1719 to move from the base 1723 of reservoir 1703 towards the drive assembly 1705. The piston 1719 may move through a lumen of reservoir 1703, along a longitudinal axis defined by reservoir 1703 (e.g., where the longitudinal axis may be analogous to axis x of FIG. 1).

The base 1723 of reservoir 1703 may include a connector 1725 configured to receive a manifold, e.g., a manifold of a patient therapy unit. Connector 1725 may include a valve to control pressure, e.g., so that pump 1700 does not immediately "lose" pressure, even if a manifold is not yet attached to the connector. The valve may include a one-way valve, configured to permit fluid into (but not out of) reservoir 1703. When the piston 1719 moves through the reservoir 1703, fluid may be drawn from the patient therapy unit into the reservoir 1703. Piston 1719 may form a barrier between the fluid of the reservoir 1703, and the drive assembly 1705.

Pump 1700 may be assembled during manufacturing such that spring 1711 is energized and piston 1719 is at the base 1723 of reservoir 1703. The spring output drum 1713 may be locked in position (described in connection to FIGS. 14E and 14F) such that cable 1717 is slack. When the pump 1700 is ready for use, a user may attach a manifold to the connector 1725 and press button 1707. Pressing button 1707 may unlock drive assembly 1705, causing torque on the output drum 1713 to create tension in cable 1717. The tension in cable 1717 may cause an upward force on the piston 1719, drawing the piston 1719 through the reservoir 1703. The force may remain constant as the spring 1711 unwinds and the cable 1717 winds onto output drum 1713. The motion of the piston 1719 may create a constant negative pressure and draw fluid from the manifold through the valve in connector 1725 into the reservoir 1703. When the reservoir 1703 is full and/or the desired amount of fluid removed from the target site, a user may disconnect the manifold from connector 1725.

Figure 14C:
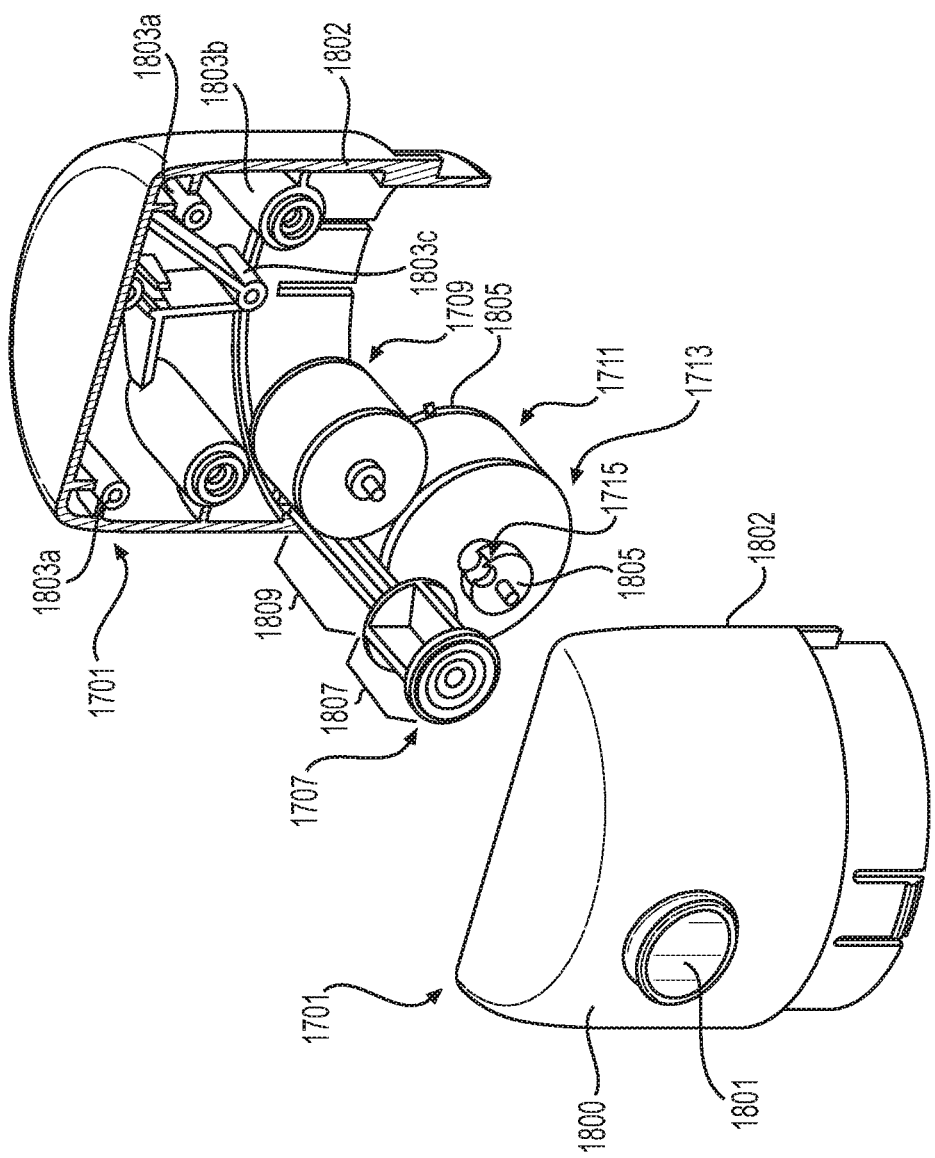
FIGS. 14C and 14D provide exploded views of an exemplary drive assembly of the negative pressure pumps of FIGS. 14A and 14B, according to one embodiment of the present disclosure.
Figure 14D:
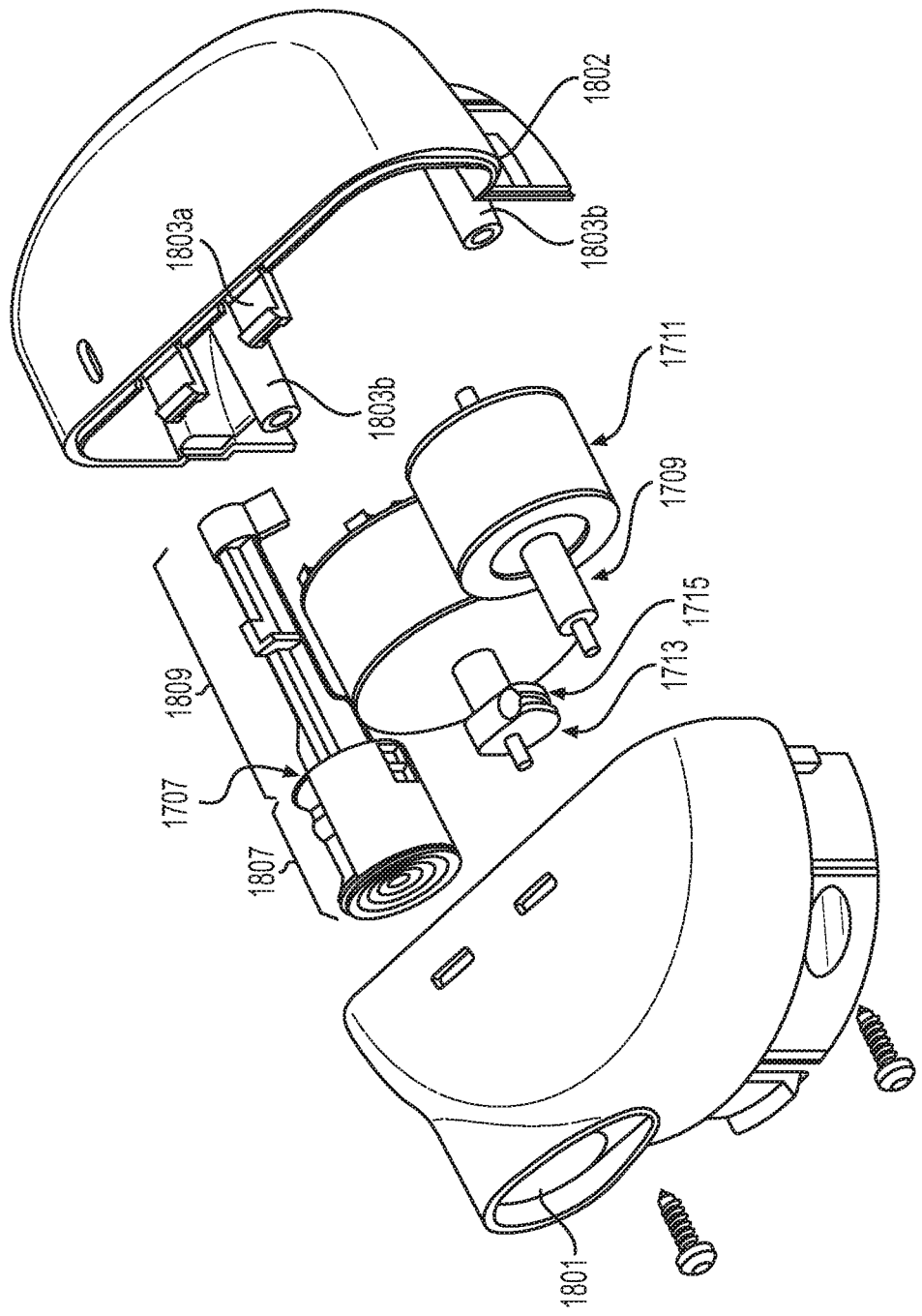

FIGS. 14C and 14D provide exploded views of an exemplary drive assembly of the negative pressure pump of FIGS. 14A and 14B. As shown in FIGS. 14C and 14D, drive assembly housing 1701 may include two discrete halves, each half having an outer surface 1800 and an edge surface 1802. The halves of drive assembly housing 1701 may be joined together at their edge surfaces 1802 by mating housing fixtures 1803a in each half, or via any other suitable method of permanent or releasable engagement. Drive assembly housing 1701 may also include a discrete, compressible member 1801. An outer surface of member 1801 may be accessible to a user. Meanwhile, an inner surface of member 1801 may abut button 1707, e.g., inaccessible to a user. Drive assembly housing 1701 may include fixtures 1803a, 1803b, and 1803c inside the inner surface of drive assembly housing 1701. Fixtures 1803a may align the two halves of drive assembly housing 1701 and assist in securing the two halves to one another. Fixtures 1803b may further position the two halves of drive assembly housing 1701, position storage drum 1709 and output drum 1713, and/or provide structural support to drive assembly housing 1701. Fixtures 1803c (shown in FIG. 14C) may contain spindles 1805 of storage drum 1709 and output drum 1713. The fixtures 1803b and 1803c may be configured to permit the spindles 1805 to rotate, such that storage drum 1709 and output drum 1713 may spin freely once button 1707 is activated. Button 1707 may include a head portion 1807 abutting the inner surface of member 1801, and a tail portion 1809 extending, at least, the length of output drum 1713. In at least one embodiment, tail portion 1809 may comprise an elongate member with one or more fins or ribs extending from a central, longitudinal axis of the tail portion 1809.

Figure 14E:
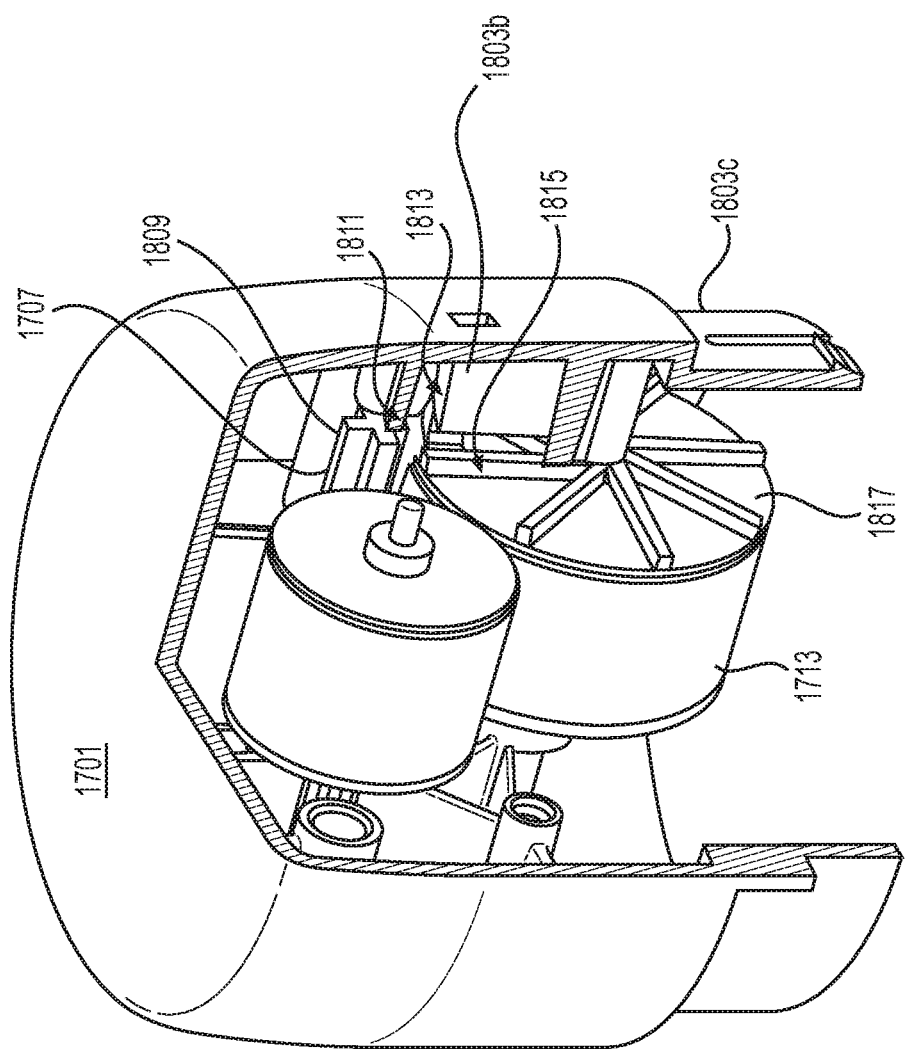
FIGS. 14E and 14F provide views of exemplary drive assembly locks of the negative pressure pumps of FIGS. 14A and 14B, according to one embodiment of the present disclosure.
Figure 14F:
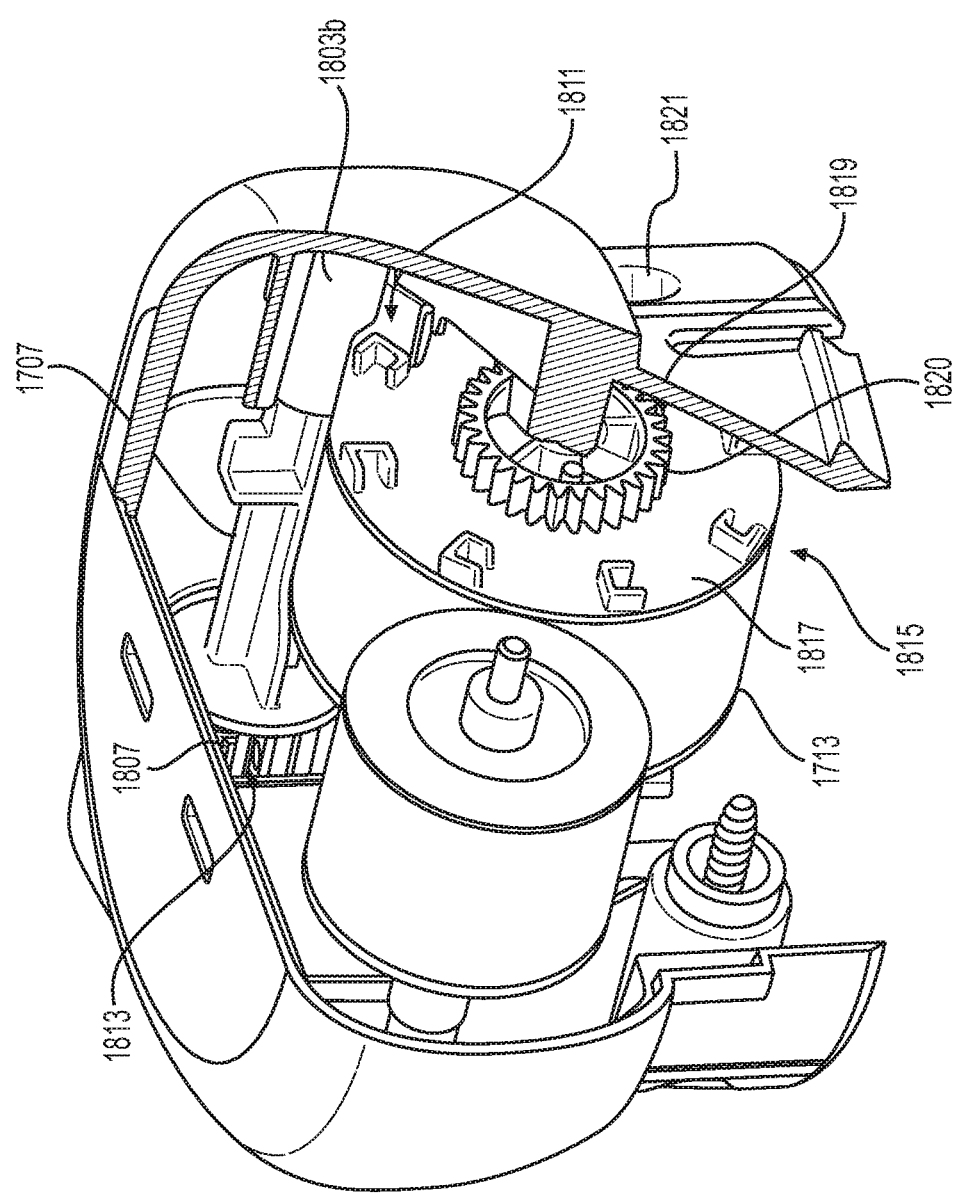

FIGS. 14E and 14F provide views of exemplary drive assembly locks of the negative pressure pump of FIGS. 14A and 14B. In the illustrated embodiments, tail portion 1809 of button 1707 includes a button lock tab 1811. The button lock tab 1811 may extend perpendicular to the longitudinal axis of the tail portion 1809 and contact the output drum 1713. FIG. 14E further provides an embodiment where the tail portion 1809 of button 1707 may include a button position detent 1813, which may extend along the longitudinal axis of the tail portion 1809 and extend into a cavity formed by a fixture 1803a of drive assembly housing 1701. FIG. 14F provides an embodiment including button position detents 1813 at a head portion 1807 of button 1707. Button position detent(s) 1813 may steady or maintain the position of button 1707. For example as shown in FIG. 14E, button 1707 may be positioned inside drive assembly housing 1701 via member 1801 engaging head portion 1807 of button 1707, and the fixture 1803c of the drive assembly housing 1701 interior containing button position detent 1813 at the tail portion 1809 of button 1707.

In at least one embodiment, output drum 1713 may include lock rib(s) 1815 which may overlap and abut button lock tab 1811. For example, output drum 1713 may comprise a cylinder with a base 1817. The base 1817 may be positioned perpendicular to the longitudinal axis of the cylinder. The base 1817 may contain rib(s), fins, or protrusion(s) which may form lock rib(s) 1815. In at least one scenario, the lock ribs 1815 may be positioned such that they are not on surface(s) of the output drum 1713 that contact the spring 1711. The lock ribs 1815 may be at equal intervals extending from the center of output drum 1713 (as shown in FIG. 14E) or along the perimeter of base 1817 (as shown in FIG. 14F). At a default position, the button lock tab 1811 may maintain the position of output drum 1713 by abutting output drum lock ribs 1815. A user may operate pump 1700 by pressing member 1801 (of FIG. 14C or FIG. 14D), thus shifting tail portion 1809 of button 1707 in the direction of housing fixture 1803c. The movement of tail portion 1809 towards housing fixture 1803c may shift button lock tab 1811 such that button lock tab 1811 no longer abuts output drum lock rib 1815. This motion may release output drum 1713 to rotate due to the pre-set bias of spring 1711. Rotation of output drum 1713 retracts cable 1717 and piston 1719 (of FIGS. 14A and 14B), allowing fluid to be drawn into reservoir 1703.

In at least one embodiment, output drum 1713 may include a single lock rib 1815. In some embodiments, output drum 1713 may include a plurality of lock ribs 1815, for example eight equally spaced ribs about output drum 1713 (as shown in FIG. 14E or FIG. 14F). The plurality of lock ribs 1815 may provide manufacturing tolerance during manufacturing of pump 1700. For example, multiple lock ribs 1815 permit output drum 1713 to rotate only until button lock tab 1811 abuts at least one drum lock rib 1815. The more lock ribs 1815 on output drum 1713, the less output drum 1713 is able to rotate before button lock tab 1811 contacts a lock rib 1815.

In at least one embodiment, pump 1700 is configured to be activated only once. For example, pump 1700 may be structured such that button 1707 does not re-engage surface 1801 and button lock tab 1811 does not re-engage rib 1815. In some embodiments, pump 1700 may be activated intermittently. For example, button 1707 may be biased to contact surface 1801, for instance, using a spring positioned at tail portion 1809. In one such scenario, pump 1700 may draw fluid into reservoir 1703 only when button 1707 is pressed. For instance, while button 1707 is pressed, button lock tab 1811 may release output drum 1713 to rotate, unwinding spring 1711 and retracting cable 1717. When button 1707 is not pressed, button lock tab 1811 may again abut an output drum lock rib 1815 and stop the rotation of output drum 1713 because button 1707 may be biased to contact surface 1801. Multiple drum lock ribs 1815 on output drum 1713 may ensure that output drum 1713 does not turn a full rotation when button 1707 is not pressed. This embodiment provides the capability for a user to start, stop, and restart fluid withdrawal into reservoir 1703, rather than only providing control regarding when to start fluid withdrawal. In at least one embodiment, the rate of rotation of output drum 1713 may be controlled, e.g., by a graded button lock tab 1811 that may vary the rotation rate of output drum 1713, depending on how far button 1707 is pressed. Such a case provides the user with the ability to control the rate of retraction of fluid into the lumen of the reservoir. In some embodiments, the retraction of cable 1717 may occur at a constant rate, such that fluid may be drawn into the reservoir at a constant rate.

As shown in FIGS. 14F and 14G, pump 1700 may include a spring winding gear 1819 and gear access hole 1821. The spring winding gear 1819 and gear access hole 1821 may permit initial activation of pump 1700, intermittent fluid withdrawal, or re-use of pump 1700. For example, spring winding gear 1819 and gear access hole 1821 may be used to wind the spring 1711 to the output drum 1713 and thus energize spring 1711. As context, spring 1711 may be wound on storage drum 1709 at a default state, prior to manufacture. The spring 1711 may be un-energized when it is on the storage drum 1709. The spring 1711 may be energized when it is wound from the storage drum 1709 to the output drum 1713 during manufacture, e.g., by using spring winding gear 1819 engaged with a pinion 1823 through gear access hole 1821, as described further below.

FIG. 14F illustrates an exemplary embodiment where spring winding gear 1819 may be positioned on the base 1817 of output drum 1713. In at least one embodiment, the spring winding gear 1819 may be coaxial with the output drum 1713 and have a smaller radius than output drum 1713. Spring winding gear 1819 may include teeth 1820 along its outer circumference.

Figure 14H:
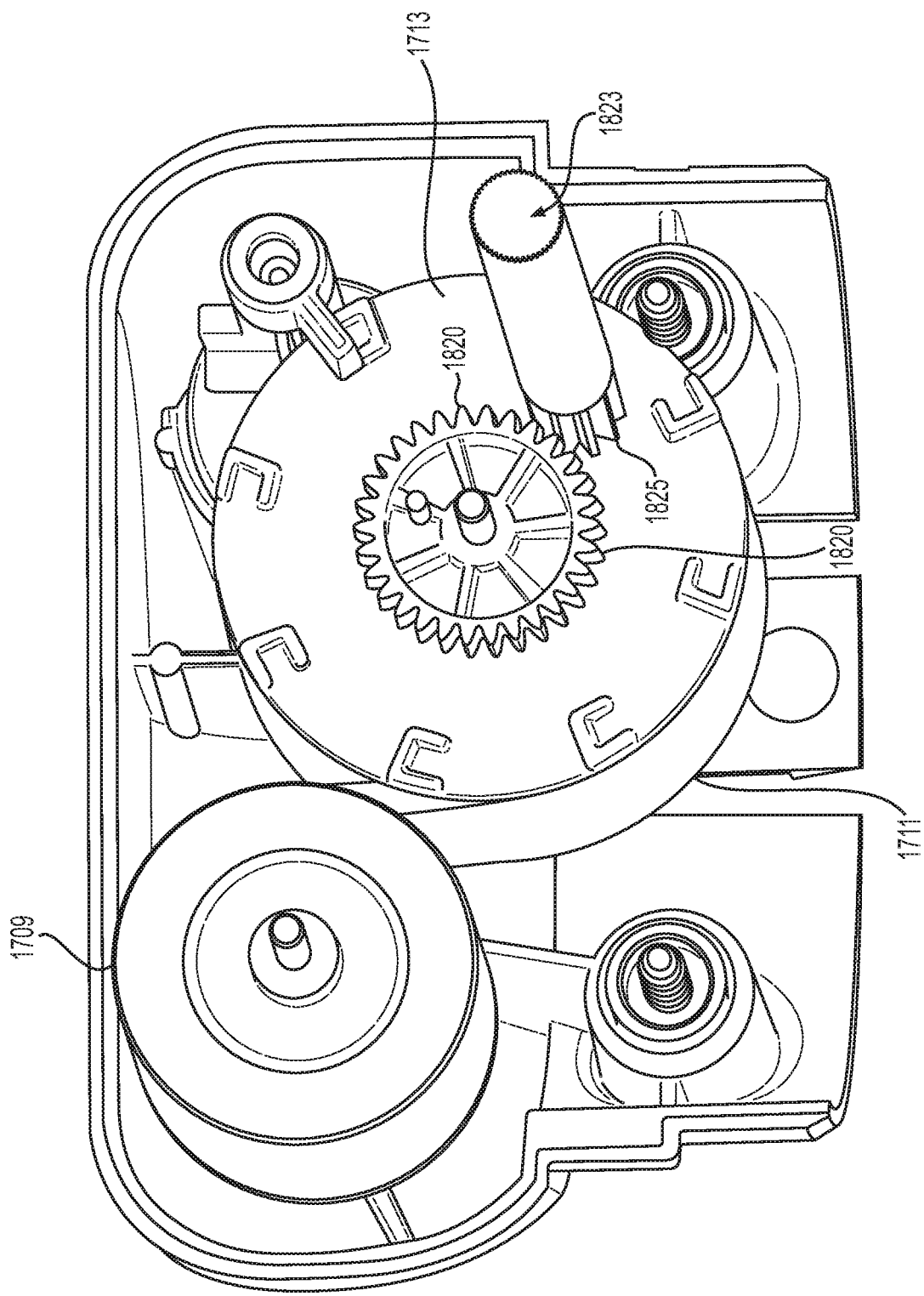

Gear access hole 1821 may be an opening in drive assembly housing 1701 (as shown in FIGS. 14F and 14G). The gear access hole 1821 may be offset from the central axis and a majority of the spring winding gear 1819 (as shown in FIG. 14G), such that a pinion 1823 inserted through the gear access hole 1821 may engage spring winding gear 1819. In particular, as shown in FIGS. 14H and 14I, pinion 1823 may comprise a cylindrical rod with interlocking teeth 1825 along at least a portion of its outer circumference. The interlocking teeth 1825 of pinion 1823 may engage teeth 1820 of the spring winding gear 1819. In at least one embodiment, turning the pinion 1823 clockwise while its interlocking teeth 1825 are engaged with teeth 1820 may wind the spring 1711 from the storage drum 1709 to the output drum 1713.

As shown in FIG. 14I, a fixture 1831 may be used to guide the pinion 1823 into gear access hole 1821, maintain the position of pinion 1823, and keep the position of pinion 1823 square with spring winding gear 1819. While FIG. 14I shows the pinion 1823 being turned by hand, any variety of winding methods may be used, including motorized winding mechanisms.

In at least one embodiment, the gear access hole 1821 may be accessible only during factory assembly of pump 1700 (e.g., inaccessible during operation by a user to remove fluid). For instance, gear access hole 1821 may be accessible only before the drive assembly housing 1701 is assembled with the reservoir 1703. In this way, the spring 1711 may only be wound during factory assembly, rather than by an end user before, during, or after user of the pump 1700. In one scenario, gear access hole 1821 may be sealed before pump 1700 leaves the factory site.

Figure 14J:
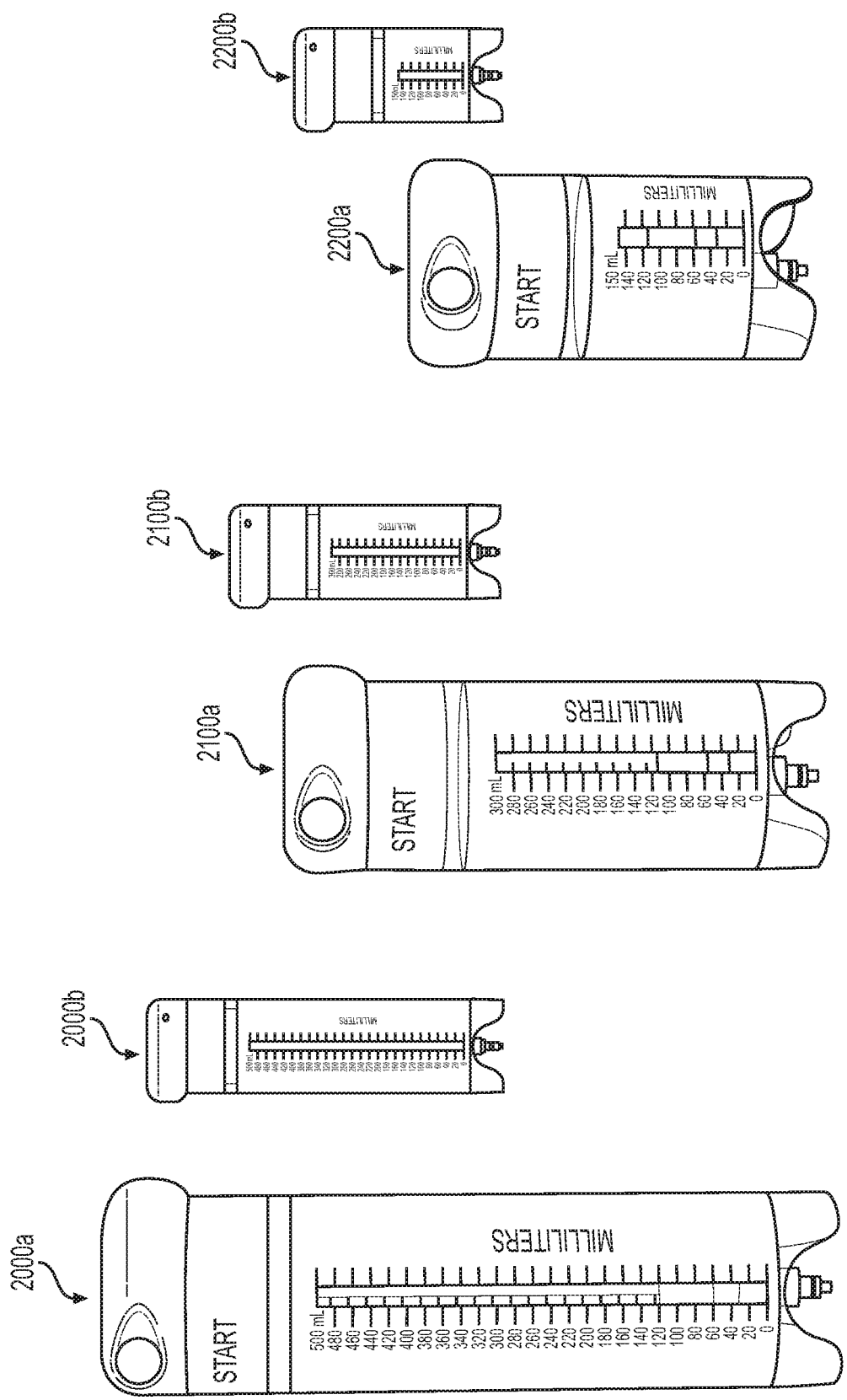
FIG. 14J provides views of various sizes of the constant torque spring driven negative pressure pumps of FIGS. 14A and 14B, according to embodiments of the present disclosure.

As shown in FIG. 14J (which depicts front and rear views of three pumps), negative pressure pump 1700 may be any variety of sizes, e.g., a 500 mL size illustrated by pump 2000a and pump 2000b, a 300 mL size illustrated by pump 2100a and pump 2100b, and a 150 mL size illustrated by pump 2200a and pump 2200b.

The description above and examples are illustrative, and are not intended to be restrictive. One of ordinary skill in the art may make numerous modifications and/or changes without departing from the general scope of the invention. For example, and as has been described, the above-described embodiments (and/or aspects thereof) may be used in combination with each other. Additionally, portions of the above-described embodiments may be removed without departing from the scope of the invention. In addition, modifications may be made to adapt a particular situation or aspect to the teachings of the various embodiments without departing from their scope. Many other embodiments will also be apparent to those of skill in the art upon reviewing the above description.

Additionally, while a number of objects and advantages of the embodiments disclosed herein (and variations thereof) are described, not necessarily all such objects or advantages may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

What is claimed is:

1. A negative pressure pump, comprising:
   a reservoir comprising an inner wall that defines a lumen along a longitudinal axis of the reservoir;
   a drive assembly coupled to the reservoir, the drive assembly comprising a spring, a first drum, and a second drum;
   a piston forming a seal against the inner wall of the reservoir and slidable within the lumen along the longitudinal axis; and
   a cable extending through the lumen, the cable having a first end coupled to the drive assembly at a cable attachment point located on the second drum and a second end coupled to the piston,
   wherein sliding the piston along the reservoir via the drive assembly creates a negative pressure within the lumen.

2. The negative pressure pump of claim 1, wherein the reservoir has a constant cross-sectional dimension along an entire length of the reservoir.

3. The negative pressure pump of claim 1, wherein the spring is coupled to the second drum.

4. The negative pressure pump of claim 1, wherein the spring is coupled to each of the first drum and the second drum.

5. The negative pressure pump of claim 4, wherein winding of the spring onto the first drum causes winding of the cable onto the second drum.

6. The negative pressure pump of claim 5, wherein the winding of the cable onto the second drum moves the piston along the longitudinal axis of the reservoir.

7. A medical system for removing fluid from a target site, comprising:
   a patient therapy unit comprising a manifold; and
   the negative pressure pump of claim 1.

8. A method of removing fluid from a target site, the method comprising:
   placing a first end of a manifold at the target site, wherein a second end of the manifold is coupled to a negative pressure pump comprising:
      a reservoir comprising an inner wall that defines a lumen along a longitudinal axis of the reservoir, the manifold being in communication with the reservoir;
      a drive assembly coupled to the reservoir and comprising a spring, a first drum, and a second drum, wherein the spring engages each of the first drum and the second drum when the drive assembly is initialized;
      a cable coupled to the second drum; and
      a piston coupled to the drive assembly, the piston having a cross-sectional dimension corresponding to a cross-sectional dimension of the reservoir; and
   initiating the drive assembly of the negative pressure pump, wherein motion of the spring moves the piston within the lumen to create a negative pressure within the reservoir.

9. The method of claim 8, wherein the piston is spaced from the drive assembly along the longitudinal axis of the reservoir before initiating the drive assembly.

10. The method of claim 8, wherein the piston is adjacent to the drive assembly after initiating the drive assembly.

11. The method of claim 8, wherein the drive assembly is coupled to the piston by the cable, and the cable extends along the longitudinal axis of the reservoir.

12. The method of claim 8, wherein the target site is an internal wound, an external wound, any location on a patient, or any location related to a patient.

13. The method of claim 8, wherein the spring comprises a torsion spring.

14. A method of manufacturing a negative pressure pump comprising a drive assembly, a reservoir, and a piston, the method comprising:
   biasing a spring of the drive assembly to wind from a first drum to a second drum,
   wherein the reservoir of the negative pressure pump comprises an inner wall that defines a lumen along a longitudinal axis of the reservoir, the drive assembly being coupled to the reservoir, and
   wherein the drive assembly is coupled to the piston by a cable extending through the lumen of the reservoir.

15. The method of claim 14, wherein biasing includes winding the spring on the second drum and locking the spring into a biased position.

16. The method of claim 14, wherein biasing the spring includes accessing a spring winding gear of the drive assembly via a gear access hole.

17. The method of claim 16, further comprising sealing the gear access hole after biasing the spring.

* * * * *